(12) United States Patent
Kim et al.

(10) Patent No.: US 9,599,653 B2
(45) Date of Patent: Mar. 21, 2017

(54) METHOD FOR DIAGNOSING INTERNAL FAULT OF OIL-IMMERSED TRANSFORMER THROUGH COMPOSITION RATIO OF DISSOLVED GAS IN OIL

(71) Applicant: HYOSUNG CORPORATION, Seoul (KR)

(72) Inventors: Sung-Wook Kim, Busan (KR); Hwang-Dong Seo, Gimhae-si (KR); Sung-Jik Kim, Gimhae-si (KR)

(73) Assignee: HYOSUNG CORPORATION, Seoul (KR)

( * ) Notice: Subject to any disclaimer, the term of this patent is extended or adjusted under 35 U.S.C. 154(b) by 207 days.

(21) Appl. No.: 14/368,677

(22) PCT Filed: Dec. 26, 2012

(86) PCT No.: PCT/KR2012/011504
§ 371 (c)(1),
(2) Date: Jun. 25, 2014

(87) PCT Pub. No.: WO2013/100591
PCT Pub. Date: Jul. 4, 2013

(65) Prior Publication Data
US 2015/0020572 A1    Jan. 22, 2015

(30) Foreign Application Priority Data

Dec. 26, 2011  (KR) .......................... 10-2011-0142842
Dec. 26, 2011  (KR) .......................... 10-2011-0142844

(51) Int. Cl.
*G01N 7/14*    (2006.01)
*G01R 31/02*   (2006.01)
(Continued)

(52) U.S. Cl.
CPC .......... *G01R 31/027* (2013.01); *G01K 13/00* (2013.01); *G01N 33/0004* (2013.01);
(Continued)

(58) Field of Classification Search
CPC ........................................................ G01N 7/14
(Continued)

(56) References Cited

U.S. PATENT DOCUMENTS 3,111,388 A * 11/1963 Horelick .................. H02H 5/08
                                                  361/37
3,680,359 A *  8/1972 Lynch .................... H01F 27/402
                                                  361/37
(Continued)

OTHER PUBLICATIONS

Park, Jin Yeub et al. "A study on failure diagnosis examples of Large oil filled transformer using dissolved gas analysis." Korean Institute of Electrical Engineers, Journal of Summer Conference, pp. 740-741 (Jul. 14, 2009).*

(Continued)

*Primary Examiner* — Clayton E Laballe
*Assistant Examiner* — Kevin Butler
(74) *Attorney, Agent, or Firm* — Novick, Kim & Lee, PLLC; Jae Youn Kim

(57) ABSTRACT

The present invention relates to a method for diagnosing an internal fault of an oil-immersed transformer by analyzing the composition ratio of dissolved gas in oil that is caused when an internal fault of the oil-immersed transformer occurs. According to the present invention, a method for diagnosing an internal fault of an oil-immersed tranformer by extracting and analyzing dissolved gas in oil from the oil-immersed transformer for which an internal fault is to be diagnosed comprises: a first step of calculating the composition ratio of each of CH4/H2, C2H2/C2H4, C2H4, C2H4/C2H6, and C2H4/CH4 from among the extracted dissolved gas in oil; a second step of determining whether the internal (Continued)

fault is an electrical fault or a thermal fault using the calculated composition ratios of CH4/H2 and C2H2/C2H4; and a third step of determining, if said internal fault is determined to be an electrical fault in the second step, whether the electrical fault is a partial discharge (PD), a discharge of low energy (D1), or a discharge of high energy (D2) using the calculated composition ratios of C2H2/C2H4 and C2H4/C2H6.

23 Claims, 11 Drawing Sheets

(51) Int. Cl.

| | | |
|---|---|---|
| *G01K 13/00* | (2006.01) | |
| *G01N 33/00* | (2006.01) | |
| *G01N 33/28* | (2006.01) | |
| G01N 33/20 | (2006.01) | |
| G01N 1/22 | (2006.01) | |
| G01N 33/24 | (2006.01) | |
| G01V 9/00 | (2006.01) | |
| G01R 31/12 | (2006.01) | |
| H01F 27/12 | (2006.01) | |

(52) U.S. Cl.
CPC ....... *G01N 33/2841* (2013.01); *G01N 1/2294* (2013.01); *G01N 7/14* (2013.01); *G01N 33/203* (2013.01); *G01N 33/24* (2013.01); *G01R 31/1281* (2013.01); *G01V 9/007* (2013.01); *H01F 27/12* (2013.01)

(58) Field of Classification Search
USPC ....................................................... 73/19.01
See application file for complete search history.

(56) References Cited

U.S. PATENT DOCUMENTS

| | | | | | |
|---|---|---|---|---|---|
| 5,243,848 | A * | 9/1993 | Cox | ................... | G01N 33/2841 73/19.05 |
| 6,289,716 | B1 * | 9/2001 | Lindgren | ........... | G01N 33/2841 73/19.1 |
| 6,568,287 | B2 * | 5/2003 | Golner | ..................... | G01N 1/14 73/863.71 |
| 8,616,045 | B2 * | 12/2013 | Cavallini | ........... | G01N 33/2841 73/19.11 |
| 8,839,658 | B2 * | 9/2014 | Herz | .................. | G01N 33/2841 73/19.01 |
| 2012/0290229 | A1 * | 11/2012 | Cavallini | ........... | G01R 31/1281 702/58 |
| 2014/0245814 | A1 * | 9/2014 | Montanari | ......... | G01N 33/2841 73/19.1 |
| 2015/0007635 | A1 * | 1/2015 | Kim | ................... | G01N 33/2841 73/19.1 |
| 2015/0020572 | A1 * | 1/2015 | Kim | ..................... | G01R 31/027 73/19.01 |

OTHER PUBLICATIONS

Park, Jeong U et al. "Consideration of the Oil-Filled Transformer Internal Fault with Dissolved Gas Analysis." Korean Institute of Electrical Engineers, Journal of Summer Conference, pp. 358-359 (Jul. 14, 2010).*
Lim, Dong Hun. "A Study on the Technique for Improving Safety by the Analysis of Correlation Between Partial Discharge and Oil Dissolved Gas of Power Transformers." Graduate School of Information Cotents, Kwangwoon University, Department of Electronics Communication Engineering, Thesis for masters degree (Jun. 2011).*
Park, Jin Yeub et al. "A study on the Reliability of Failure Diagnosis Methods of Oil Filed Transfomer using Actual Dissolve Gas Concentration.", Korean Institute of Electrical Engineers, Journal of Sep. 2011, vol. 60P, No. 3, pp. 114-119.*
Sukhbir Singh et al. "Duval Triangle" A Noble Technique for DGA in Power Transfomers. International Journal of Electrical and Power Engineering, vol. 4, Issue 3, pp. 193-197 (2010).*
Chander, Ankush et al. Failure Analysis of a Power Transformer Using Dissolved Gas Analysis—A Case Study, International Journal of Research in Engineering Technology, vol. 03 Issue: 05, May 2014, pp. 300-303.*
Agarasan, Ioana, "Monitoring and Diagnosis Methods for High Voltage Power Transformers", U.P.B. Sci. Bull., Series C, vol. 70, No. 3, 2008.*
Wang, Xiaohui, "Research on Transformer Fault Diagnosis baed on Multi-source Information Fusion", International Journal of Control and Automation, vol. 7, No. 2 (2014), pp. 197-208, http://dx.doi.org/10.14257/ijca2014.7.2.19.*
Duval, Michel et al. "Interpretation of Gas-In-Oil Analysis Using New IEC Publication 60599 and IEC TC 10 Databases", IEEE Electrical Insulation Magazine, Mar./Apr. 2001, vol. 17, No. 2, pp. 31-41.*
Hamrick, Lynn, "Dissolved Gas Analysis for Transformers", ESCO Energy Services, Winter 2009-2010, pp. 1-3.*
Dr. M.N. Bandyopadhyay, "Transfomer Diagnostics in the Practical Field", Institute of Electrical and Electronics Engineers, 2007.*
Patent Cooperation Treaty ISA, "Written Opinion of the International Searching Authority", PCT/KR2012/011504, Dec. 26, 2012.*
Lim, Bong Hun. "A Study on the Technique for Improving Safety by the Analysis of Correlation Between Partial Discharge and Oil Dissolved Gas of Power Transformers." Graduate School of Information Cotents, Kwangwoon University, Department of Electronics Communication Engineering, Thesis for master's degree (Jun. 2011).

\* cited by examiner

METHOD FOR DIAGNOSING INTERNAL FAULT OF OIL-IMMERSED TRANSFORMER THROUGH COMPOSITION RATIO OF DISSOLVED GAS IN OIL

TECHNICAL FIELD

The present invention relates to a method of diagnosing an internal fault of an oil-immersed transformer, and more particularly, to a method of accurately diagnosing an internal fault of an oil-immersed transformer by analyzing a composition ratio of dissolved gases generated when the internal fault occurs in the oil-immersed transformer.

BACKGROUND ART

An oil-immersed transformer installed in a transformer substation or an electric power plant is one of the more important components of an electric power supplying system, and it is required to have high reliability. The oil-immersed transformer may have its electrical and mechanical performance degraded due to deterioration during operation, which causes an abnormal condition of the oil-immersed transformer. This phenomenon may cause a serious accident if it may not be detected in advance and appropriately treated.

When an abnormal phenomenon such as dielectric breakdown, local overheating, and the like occurs in the oil-immersed transformer, this phenomenon always accompanies a generation of heat. An insulating material, such as insulating oil, an insulating paper, pressboard, and the like, contacting a heat-generating source is affected by the heat and dissolved by a chemical reaction to generate gases. Most of these gases are dissolved in the insulating oil. Therefore, when gases are extracted and analyzed from the insulating oil taken from the oil-immersed transformer, a type and an extent of the fault occurring in the transformer may be diagnosed.

The type of the internal faults in the oil-immersed transformer and the method of diagnosing the internal fault of the oil-immersed transformer through the dissolved gases are prescribed in the international standard (IEC 60599: Mineral oil-impregnated electrical equipment in service guide to the interpretation of dissolved and free gases analysis and IEEE C57.104: IEEE Guide for the interpretation of gases in oil-immersed transformer), and most electric power companies and users of oil-immersed electric power devices estimate the internal fault depending on the international standard.

The type of fault prescribed in these international standards is classified into an electrical fault and a thermal fault, and particularly, into six faults such as partial discharges, discharges of low energy D1, discharges of high energy D2, a first thermal fault (thermal fault t<300° C.) T1, a second thermal fault (300° C.<thermal fault t<700° C.) T2, and a third thermal fault (thermal fault t>700° C.) T3. Further, gases which are objects to be analyzed in the international standards include five components such as hydrogen H2, methane CH4, ethane C2H2, ethylene C2H4, and acetylene C2H2.

Conventionally, the type of fault is classified by analyzing a composition ratio of the five gases, a content ratio of each of the five gases, a range of a key gas, and the like. However, in the conventional method of diagnosing the internal fault of the oil-immersed transformer, there are problems as follows.

First, in the diagnosis method using the key gas, since the fault is diagnosed by using only the key gas (a maximum gas value), a pattern, a composition, and a variation according to energy in each fault cannot be applied to the diagnosis method, resulting in an increase in a ratio of a wrong diagnosis. For example, if not the key gas but another gas has the maximum value, there is a problem in that there is present a region in which the diagnosis is impossible.

On the other hand, in the diagnosis method using the composition ratio of the five gases, since a result of the diagnosis is established by applying the pattern, the composition, and the variation of the gas to the diagnosis, an accuracy of the diagnosis is higher. However, it is impossible to diagnose the internal fault of the transformer when the internal fault does not fall within the type of the fault and a ratio of gas in each fault.

Meanwhile, in the diagnosis method using the content ratio of the gas, there is no region in which the diagnosis is impossible, and the accuracy of the diagnosis is higher. However, only three gases having high energy of the fault are used, and hydrogen and ethane generated in the low energy fault are not applied to the diagnosis. Accordingly, there is a problem in that it is difficult to diagnose an initial fault.

Therefore, there is required development of a technology to diagnose the internal fault of the oil-immersed transformer, in which reliability of the diagnosis for the internal fault of the oil-immersed transformer can be improved and all kinds of faults can be diagnosed.

DISCLOSURE OF THE INVENTION

Technical Problems

The present invention has been developed to solve the above-mentioned problems in the conventional art, and an aspect of the present invention is to provide a method of diagnosing an internal fault of an oil-immersed transformer through a composition ratio of a dissolved gas, which is capable of accurately diagnosing the internal fault of the oil-immersed transformer by using the composition ratio of the dissolved gas generated when the internal fault of the oil-immersed transformer occurs.

Further, another aspect of the present invention is to provide a method of diagnosing an internal fault of an oil-immersed transformer through a composition ratio of a dissolved gas, which is capable of determining the internal fault by steps according to the composition ratio of the dissolved gas depending on each fault by classifying the internal fault of the oil-immersed transformer into an electrical fault and a thermal fault.

Means to Solve the Problem

In accordance with the first embodiment of the present invention, there is provided a method of diagnosing an internal fault of an oil-immersed transformer by extracting and analyzing dissolved gases from the oil-immersed transformer of which the internal fault is able to be diagnosed. The method includes: a first step of calculating composition ratios of CH4/H2, C2H2/C2H4, C2H4/C2H6, and C2H4/CH4 among the dissolved gases which are extracted; a second step of determining whether the internal fault is an electrical fault (E) or a thermal fault (T) by making CH4/H2 and C2H2/C2H4, which are already calculated, to correspond to an internal fault region which is preset; and a third step of determining whether the internal fault is a partial discharge (PD), a low energy discharge (D1), or a high energy discharge (D2) by making C2H2/C2H4 and C2H4/C2H6, which are previously calculated, to the internal fault region which is preset, if the internal fault is the electrical fault (E) as a result of the determination in the second step.

In the embodiment, the second step includes: setting CH4/H2 and C2H2/C2H4, which are indicated depending on each of the electric fault and the thermal fault in each of a plurality of oil-immersed transformers of which a type of the internal fault is known, as x and y coordinates on a first xy-plane; and classifying a whole region of the first xy-plane into the electric fault (E) and the thermal fault (T) by using the plurality of x and y coordinates which are set, wherein it is determined whether the internal fault is the electric fault (T) or the thermal fault (E) by using a region corresponding to the plural coordinates for CH4/H2 and C2H2/C2H4 which are calculated in the first step.

In the embodiment of the present invention, the third step includes: setting C2H2/C2H4 and C2H4/C2H6, which are indicated depending on each of the partial discharge (PD), the high energy discharge (D1), and the low energy discharge (D2) in each of a plurality of oil-immersed transformers in which the electric fault occurs, as x and y coordinates on a second xy-plane; and classifying a whole region of the second xy-plane into the partial discharge (PD), the low energy discharge (D1), and the high energy discharge (D2) by using the plurality of x and y coordinates which are set, wherein it is determined whether the internal fault is the partial discharge (PD), the low energy discharge (D1), or the high energy discharge (D2), by using the region corresponding to the plural coordinates for C2H2/C2H4 and C2H4/C2H6 which are calculated in the first step.

In the embodiment of the present invention, the method of diagnosing the internal fault of the oil-immersed transformer further includes: a fourth step of determining whether the internal fault is the first thermal fault (t<300° C.) (T1), the second thermal fault (300° C.<t<700° C.) (T2), or the third thermal fault (t>700° C.) (T3), by using C2H4/C2H6 and C2H4/CH4 which are calculated, if the internal fault is the thermal fault (T) as a result of the determination in the second step; and a fifth step of determining whether the internal fault is the second thermal fault (300° C.<t<700° C.) (T2) or the third thermal fault (t>700° C.) (T3), by using C2H2/C2H4 and C2H4/C2H6, if the internal fault is the second thermal fault (300° C.<t<700° C.) (T2) or the third thermal fault (t>700° C.) (T3) as a result of the determination in the fourth step.

In the embodiment of the present invention, the fourth step includes: setting C2H4/C2H6 and C2H4/CH4, which are indicated depending on the first thermal fault (t<300° C.), the second thermal fault (300° C.<t<700° C.) (T2), or the third thermal fault (t>700° C.) (T3) in each of the plurality of oil-immersed transformers of which the thermal fault occurs, as the x and y coordinates on a third xy-plane; and classifying a whole region of the third xy-plane a first thermal region (T1), a second thermal fault, or a third thermal fault by using the x and y coordinates which are set, wherein it is determined whether the internal fault is the first thermal fault (T1), the second thermal fault, or the third thermal fault, by using a region corresponding to the plural coordinates for C2H4/C2H6 and C2H4/CH4 which are calculated in the first step.

In the embodiment of the present invention, the fifth step includes: setting C2H4/C2H4 and C2H4/C2H6, which are indicated depending on the second thermal fault (300° C.<t<700° C.) (T2) and the third thermal fault (t>700° C.) (T3) in each of the plurality of oil-immersed transformers of which a type of the internal faults is known, as the x and y coordinates on the fourth xy-plane; and classifying a whole region of the fourth xy-plane into the second thermal fault (T2) region and the third thermal fault (T3) region by using the x and y coordinates which are set, wherein it is determined whether the internal fault is the second thermal fault or the third thermal fault, by using a region corresponding to the plural coordinates for C2H2/C2H4 and C2H4/C2H6 which are calculated in the first step.

In accordance with the first embodiment of the present invention, there is provided a method of diagnosing an internal fault of an oil-immersed transformer through a composition ratio of a dissolved gas in oil. The method includes: a first step of calculating composition ratios of CH4/H2, C2H2/C2H4, C2H4/C2H6, and C2H4/CH4 of dissolved gases after extracting the dissolved gases from each of a plurality of oil-immersed transformers of which the internal fault is known; a second step of classifying a whole region of the first xy-plane into an electrical fault (E) and a thermal fault (T) by using a plurality of x and y coordinates after setting CH4/H2 and C2H2/C2H4, which are indicated depending on each of the electrical fault (E) and the thermal fault (T) among the internal faults, as the x and y coordinates on the first xy-plane; a third step of classifying a whole region of a second xy-plane into a partial discharge (PD) region, a low energy discharge (D1) region, and a high energy discharge (D2) region by using the plural x and y coordinates after setting C2H2/C2H4 and C2H4/C2H6, which are indicated depending on each of a partial discharge (PD), a low energy discharge (D1), and a high energy discharge (D2) among the internal faults, as the x and y coordinates on the second xy-plane; a fourth step of classifying a whole region of a third xy-plane into a first thermal fault (T1) region, a second thermal fault (T2) region, and a third thermal fault (T3) region after setting C2H4/C2H6 and C2H4/CH4, which are indicated depending on each of a first thermal fault (t<300° C.) (T1), a second thermal fault (300° C.<t<700° C.) (T3), and a third thermal fault (t>700° C.) (T3) of the thermal fault (T), as the x and y coordinates on the third xy-plane; a fifth step of classifying a whole region of a fourth xy-plane into the second thermal fault (T2) region and the third thermal fault (T3) region by using a plurality of x and y coordinates after setting C2H2/C2H4 and C2H4/C2H6, which are indicated depending on each of the second thermal fault (300° C.<t<700° C.) (T3) and the third thermal fault (t>700° C.) (T3), as the x and y coordinates on the third xy-plane respectively; a sixth step of calculating composition ratios of CH4/H2, C2H2/C2H4, C2H4/C2H6, and C2H4/CH4 among the dissolved gases which are extracted from the oil-immersed transformer for diagnosis, of which the internal fault is able to be diagnosed; and a seventh step of determining a region, which corresponds to the x and y coordinates of two selected from CH4/H2, C2H2/C2H4, C2H4/C2H6, and C2H4/CH4 which are calculated, on the first to fourth xy-planes, so as to determine a type of the internal fault of the oil-immersed transformer to be diagnosed, by using the determined region.

In the embodiment of the present invention, the seventh step determines a region, which corresponds to plural coordinates for CH4/H2 and C2H2/C2H4 which are calculated in the sixth step, on the first xy-plane, so as to determine whether the internal fault is the electric fault (E) or the thermal fault (T) by using the determined region.

In the embodiment of the present invention, the seventh step includes: determining a region, which corresponds to plural coordinates for C2H2/C2H4 and C2H4/C2H6 calculated in the sixth step, on the second xy-plane if it is determined that the internal fault is the electrical fault (E), so as to determine whether the electrical fault is a partial discharge (PD), a low energy discharge (D1), or a high energy discharge (D2), by using the determined region.

In the embodiment of the present invention, the seventh step includes: determining a region, which corresponds to plural coordinates for C2H4/C2H6 and C2H4/CH4 calculated in the sixth step, on the third xy-plane if it is determined that the internal fault is the thermal fault (T), so as to determine whether the thermal fault (T) is a first thermal fault (t<300° C.) (T1), a second thermal fault (300° C.<t<700° C.) (T2), or a third thermal fault (t>700° C.) (T3), by using the determined region.

In the embodiment of the present invention, a region, which corresponds to the x and y coordinate for C2H2/C2H4 and C2H4/C2H6 calculated in the sixth step, is determined on the fourth xy-plane if it is determined that the thermal fault is the second thermal fault (300° C.<t<700° C.) (T2) or the third thermal fault (t>700° C.) (T3), so as to determine whether the thermal fault is the second thermal fault (300° C.<t<700° C.) (T2) or the third thermal fault (t>700° C.) (T3) by using the determined region.

In the embodiment of the present invention, the electrical fault region of the whole region of the first xy-plane simultaneously satisfies a condition of CH4/H2<0.5 and C2H2/C2H4>0.4, and a condition of CH4/H2<3 and C2H2/C2H4>0.4, while the thermal fault region simultaneously satisfies a condition of CH4/H2>0.5 and C2H2/C2H4≤0.4, and a condition of CH4/H2>3 and C2H2/C2H4>0.4.

In the embodiment of the present invention, the partial discharge (PD) region of the whole region of the second xy-plane satisfies a condition of C2H2/C2H4≤2 and C2H4/C2H6≤0.1, the low energy discharge (D1) region simultaneously satisfies a condition of C2H2/C2H4>2 and C2H4/C2H6≤1.5, a condition of C2H2/C2H4≤2 and 0.1<C2H4/C2H6≤1.5, and a condition of C2H2/C2H4>2.5 and C2H4/C2H6>1.5, and the high energy discharge (D2) region satisfies a condition of C2H2/C2H4≤2.5 and C2H4/C2H6>1.5.

In the embodiment of the present invention, the first thermal fault (t<300° C.) (T1) region of the whole region of the third X-Y plane simultaneously satisfies a condition of C2H4/C2H6≤0.2 and C2H4/CH4≤0.2, and a condition of C2H4/C2H6>0.2 and 0.05<C2H4/CH4≤0.2, and the second thermal fault (300° C.<t<700° C.) (T2) or the third thermal fault (t>700° C.) regions simultaneously satisfy a condition of C2H4/C2H6>0.2 and C2H4/CH4≤0.05 and a condition of C2H4/CH4>0.2.

In the embodiment of the present invention, in the whole region of the fourth X-Y plane, the second thermal fault (300° C.<t<700° C.) (T2) region simultaneously satisfies a condition of C2H2/C2H4>0.0005 and C2H4/C2H6≤2, and a condition of 0.0005<C2H2/C2H4≤0.02 and 2<C2H4/C2H6≤4.68, and the third thermal fault (t>700° C.) (T3) region simultaneously satisfies a condition of C2H2/C2H4≤0.0005, a condition of 0.0005<C2H2/C2H4≤0.02 and C2H4/C2H6>4.68, and a condition of C2H2/C2H4>0.02 and C2H4/C2H6>2.

In accordance with the second embodiment of the present invention, further there is provided a method of diagnosing an internal fault of an oil-immersed transformer by extracting and analyzing dissolved gases from the oil-immersed transformer of which the internal fault is able to be diagnosed. The method includes: a first step of calculating CH4/H2 and C2H2/CH4 in the dissolved gases which are extracted; and a second step of making CH4/H and C2H2/CH4, which are calculated, to correspond to a preset internal fault region, so as to determine whether the internal fault is a thermal fault (T), or a partial discharge (PD) or an energy discharge (D1 or D2) of an electrical fault (E).

In the embodiment of the present invention, the second step includes: setting CH4/H2 and C2H2/CH4, which are indicated depending on the thermal fault (T), or each of the partial discharge (PD) and the energy discharge (D1 or D2) of the electric fault (E) in each of a plurality of oil-immersed transformers of which a type of internal fault is known, as x and y coordinates on a fifth xy-plane in advance; and classifying a whole region of the fifth xy-plane into a thermal fault (T) region, and the partial discharge (PD) region and the energy discharge (D1 or D2) region of the electric fault (E), wherein it is determined whether the electric fault (E) is the partial discharge (PD) or the energy discharge (D1 or D2) by using a region corresponding to the plural coordinates for CH4/H2 and C2H2/C2H4 which are calculated in the first step.

In accordance with the second embodiment of the present invention, further, there is provided a method of diagnosing an internal fault of an oil-immersed transformer by extracting and analyzing dissolved gases from the oil-immersed transformer of which the internal fault is able to be diagnosed. The method includes: a first step of calculating C2H4/C2H6 and C2H2/C2H4 in the extracted and dissolved gases; and a second step of determining whether the internal fault is a partial discharge (PD), a low energy discharge (D1), or a high energy discharge (D2) of an electric fault (E), or a first thermal fault (t<300° C.) (T1), a second thermal fault (300° C.<t<700° C.) (T2), or a third thermal fault (t>700° C.) (T3).

In the embodiment of the present invention, the second step includes: setting C2H4/C2H6 and C2H2/C2H4, which are indicated depending on each of the partial discharge (PD), the low energy discharge (D1), and the high energy discharge (D2) of the electric fault (E), and the first thermal default (t<300° C.) (T1), the second thermal default (300° C.<t<700° C.) (T2), and the third thermal default (t>700° C.) (T3) in each of a plurality of oil-immersed transformers of which a type of internal faults is known, as x and y coordinates on a sixth xy-plane; and classifying a whole region of the sixth xy-plane into a partial discharge (PD) region, a low energy discharge (D2) region, a high energy discharge (D3) region, a first thermal fault (T1) region, a second thermal fault (T2) region, a third thermal fault (T3) region, wherein it is determined whether the internal fault is the partial discharge (PD), the low energy discharge (D2), the high energy discharge (D3), the first thermal fault (T1), the second thermal fault (T2), and the third thermal fault (T3).

In accordance with the second embodiment of the present invention, there is provided a method of diagnosing an internal fault of an oil-immersed transformer through composition ratios of dissolved gases. The method includes: a first step of calculating CH4/H2 and C2H2/CH4 in the dissolved gases after extracting the dissolved gases from each of a plurality of transformers of which a type of internal fault is known; a second step of setting CH4/H2 and C2H2/CH4, which are indicated depending on each of a thermal fault (T), and a partial discharge (PD) and an energy discharge (D1 or D2) of an electrical fault (E), as x and y coordinates on a fifth xy-plane, so as to classify a whole region of the fifth xy-plane into a thermal fault (T) region, a partial discharge (PD) region, and an energy discharge (D1 or D2) region by using the plurality of x and y coordinates which are set; a third step of extracting the dissolved gases from insulating oil of the oil-immersed transformer of which the internal fault is able to be diagnosed, so as to calculate CH4/H2 and C2H2/CH4 in the dissolved gases; and determining the x and y coordinates consisting of CH4/H2 and C2H2/CH4 which are calculated in the third step, so as to determine whether the internal fault of the oil-immersed transformer to be diagnosed is the thermal fault (T), the partial discharge (PD), or the energy discharge (D1 or D2) by using the determined region.

In the embodiment of the present invention, in the whole region of the fifth X-Y plane, the thermal fault region is 2<CH4/H2 and 0.3<C2H2/CH4, 0.01<C2H2/CH4≤0.3, or 1<CH4/H2 and C2H2/CH4≤0.01, the partial discharge (PD) region CH4/H2≤1 and C2H2/CH4≤0.01, and the energy discharge (D1 or D2) region is CH4/H2≤2 and 0.3<C2H2/CH4.

In accordance with the second embodiment of the present invention, there is provided a method of diagnosing an internal fault of an oil-immersed transformer through a composition ratio of dissolved gases. The method includes: a first step of calculating C2H4/C2H6 and C2H2/C2H4 in the dissolved gases after extracting the dissolved gases from each of a plurality of transformers of which a type of internal faults is known; a second step of setting C2H4/C2H6 and C2H2/C2H4, which are indicated depending on each of a partial discharge (PD), a high energy discharge (D1), and a low energy discharge (D2) of an electric fault (E), and a first thermal fault (t<300° C.) (T1), a second thermal fault (300° C.<t<700° C.) (T2), and a third thermal fault (t>700° C.) (T3) of a thermal fault (T) among the internal faults, as x and y coordinates on a sixth xy-plane, so as to classify a whole region of the sixth xy-plane into a partial discharge (PD) region, a low energy discharge (D1) region, a high energy discharge (D2) region, a first thermal fault (t<300° C.) (T1) region, a second thermal fault (300° C.<t<700° C.) (T2) region, and a third thermal fault (t>700° C.) (T3) by using a plurality of coordinates which are set; a third step of extracting the dissolved gases from insulating oil of the oil-immersed transformer of which the internal fault is able to be diagnosed, so as to calculate C2H4/C2H6 and C2H2/C2H4 in the dissolved gases; and a fourth step of determining x and y coordinates consisting of C2H4/C2H6 and C2H2/C2H4 which are calculated in the third step, so as to determine whether the internal fault of the oil-immersed transformer to be diagnosed is the partial discharge (PD), the low energy discharge (D1), the high energy discharge (D2), the first thermal fault (t<300° C.) (T1), the second thermal fault (300° C.<t<700° C.) (T2), or the third thermal fault (t>700° C.) (T3) by using the determined region.

Advantageous Effects

According to the present invention, a ratio of a wrong diagnosis of the internal fault in the oil-immersed transformer can be reduced.

Further, according to the present invention, since there is no region in which the diagnosis cannot be performed when diagnosing the internal fault of the oil-immersed transformer, the reliability of the diagnosis of the internal fault can be improved.

BEST MODE

Hereinafter, exemplary embodiments of the present invention will be described with reference to the accompanying drawings. In the following description of the present invention, a detailed description of known functions and configurations incorporated herein will be omitted when it may make the subject matter of the present invention rather unclear.

Figure 1:
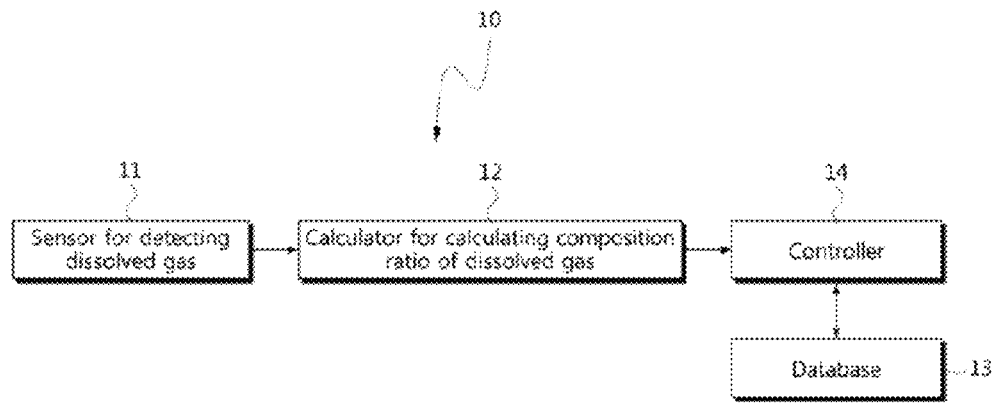
FIG. 1 is a block diagram illustrating a configuration of an apparatus for diagnosing an internal fault of an oil-immersed transformer to which the present invention is applied.

FIG. 1 is a block diagram illustrating a configuration of an apparatus for diagnosing an internal fault of an oil-immersed transformer to which the present application is applied.

Referring to FIG. 1, the apparatus of diagnosing the internal fault of the oil-immersed transformer 10 includes a sensor 11 for detecting dissolved gases, a calculator 12 for calculating content ratios of the dissolved gases, a database (DB) 13, and a controller 14.

The sensor 11 for detecting the dissolved gases detects the dissolved gases contained in insulating oil in the oil-immersed transformer. The sensor 11 for detecting the dissolved gases includes an extractor for extracting the dissolved gases dissolved in the insulating oil of the oil-immersed transformer, and a detector for determining a magnitude of the dissolved gases extracted from the insulating oil. In the embodiment, the sensor 11 for detecting the dissolved gas extracts hydrogen H2, methane CH4, acetylene C2H2, ethylene C2H4, and ethane C2H6 from the plurality of dissolved gases, and measures a quantity of each gas. CH4 and C2H6 among these five dissolved gases are classified as a low temperature fault, C2H4 is classified as a high temperature fault, H2 is classified as a low energy discharge, and C2H2 is classified as a high energy discharge.

The calculator 12 for calculating composition ratios of the dissolved gases calculates composition ratios of CH4/H2, C2H2/CH4, C2H4/C2H6, and C2H2/C2H4 selected from five dissolved gases which are detected by the sensor 11 for detecting the dissolved gases. Herein, for example, CH4/H2 indicates a composition ratio of CH4 to H2.

The database (DB) 13 stores data which is reference information used to determine the internal fault of the immersed transformer. More particularly, in the first embodiment of the present invention, the database (DB) 13 stores a first xy-plane view on which CH4/H2 and C2H2/

C2H4 are defined as an x-axis and a y-axis, a second xy-plane view on which C2H2/C2H4 and C2H4/C2H6 are defined as an x-axis and a y-axis, a third xy-plane view on which C2H4/C2H6 and C2H4/CH4 are defined as an x-axis and a y-axis, a fourth xy-plane view on which C2H2/C2H4 and C2H4/C2H6 are defined as an x-axis and a y-axis, and various data related to each plane view. For example, a fault region is classified according to a type of the internal fault. At this time, the four plane views are used to determine a type of the internal fault by using the composition ratios of CH4/H2, C2H2/C2H4, C2H4/C2H6, and C2H4/CH4 calculated in the oil-immersed transformer for a diagnosis, of which the internal fault is able to be diagnosed. Values of CH4/H2, C2H2/C2H4, C2H4/C2H6, and C2H4/CH4 are detected from each of a plurality of oil-immersed transformers of which a type of the internal fault is known, and the composition ratios of CH4/H2 and C2H2/C2H 4, C2H2/C2H4 and C2H4/C2H6, C2H4/C2H6 and C2H4/CH 4, and C2H2/C2H4 and C2H4/C2H6, which are calculated by using the values, are preset as x and y coordinates on the first to fourth xy-planes, and regions are divided depending on the type of the internal fault by using each of a plurality of x and y coordinates set as described above.

Further, in the second embodiment of the present invention, the database (DB) 13 stores a fifth xy-plane view on which CH4/H2 and C2H2/CH4 are defined as an x-axis and a y-axis respectively, a sixth xy-plane view on which C2H4/C2H6 and C2H2/C2H4 are defined as an x-axis and a y-axis, and various data related to these plane views. For example, a fault region is classified according to a type of the internal fault. At this time, the two plane views are used to determine a type of the internal fault by using the composition ratios of CH4/H2, C2H2/C2H4, C2H4/C2H6, and C2H4/CH4 calculated in the oil-immersed transformer for a diagnosis, of which the internal fault is able to be diagnosed. CH4/H2 and C2H2/CH4, and C2H4/C2H6 and C2H2/C2H4, which are calculated from five dissolved gases of H2, CH4, C2H2, C2H4, and C2H6 detected in a plurality of oil-immersed transformers of which a type of the internal fault is known, are preset as x and y coordinates on the fifth and sixth xy-planes, and regions are classified depending on the type of the internal fault by using each of the x and y coordinates set as described above.

The controller 14 determines the internal fault of the corresponding oil-immersed transformer for the diagnosis by using CH4/H2 and C2H2/C2H4, C2H2/C2H4 and C2H4/C2H6, C2H4/C2H6 and C2H4/CH4, and C2H2/C2H4 and C2H4/C2H6 calculated for the oil-immersed transformer for the diagnosis, of which the internal fault is able to be determined in the first embodiment. Particularly, the controller 14 according to the first embodiment of the present invention defines CH4/H2 and C2H2/C2H4, C2H2/C2H4 and C2H4/C2H6, C2H4/C2H6 and C2H4/CH4, C2H2/C2H4 and C2H4/C2H6, which are composition ratios of the dissolved gases detected in the oil-immersed transformer for the diagnosis, as an x-axis and a y-axis respectively, and determines which fault region the x and y coordinates correspond to in the first to fourth xy-planes stored in the database (DB) 13, so as to finally determine a corresponding internal fault. Further, the controller 14 determines whether the internal fault is an electrical fault (E) or a thermal fault (T), by using CH4/H2 and C2H2/C2H4. As a result of the determination, if the internal fault is the electrical fault (E), the controller 14 determines whether the internal fault is a partial discharge (PD), a low energy discharge (D1), or a high energy discharge (D2), by using C2H2/C2H4 and C2H4/C2H6. As a result of the determination, if the internal fault corresponds to the thermal fault (T), the controller 14 determines whether the internal fault is a first thermal fault (t<300° C.) (T1), a second thermal fault (300° C.<t<700° C.) (T2), or a third thermal fault (t>700° C.) (T3), by using C2H4/C2H6 and C2H4/CH4. At this time, more particularly, the controller determines whether the internal fault corresponds to the second thermal fault (300° C.<t<700° C.), or the third thermal fault (t>700° C.) (T3), by using C2H2/C2H4 and C2H4/C2H6.

In addition, the controller 14 determines the internal fault of the oil-immersed transformer for the diagnosis by using CH4/H2 and C2H2/CH4, and C2H4/C2H6 and C2H2/C2H4, which are calculated for the oil-immersed transformer for the diagnosis, of which the internal fault is able to be determined in the second embodiment. Particularly, the controller 14 according to the second embodiment of the present invention defines CH4/H2 and C2H2/CH4, and C2H4/C2H6 and C2H2/C2H4, which are the composition ratios of the dissolved gases detected from the oil-immersed transformer for the diagnosis, as the x and y coordinates respectively, and determines fault region in the fifth and sixth xy-planes stored in the database (DB) 13, to which each of the x and y coordinates corresponds. Finally, the controller 14 determines the corresponding internal fault. More particularly, the controller 14 may determine whether the internal fault is the thermal fault T, or the partial discharge (PD) or the energy discharge (D1, or D2) of the electrical fault (E), by using CH4/H2 and C2H2/CH4, and further may determine whether the internal fault is the partial discharge (PD), the low energy discharge (D1), or the high energy discharge (D2) of the electrical fault (E), or the first thermal fault (t<300° C.) (T1), the second thermal fault (300° C.<t<700° C.), or the third thermal fault (t>700° C.) (T3) of the thermal fault (T) by using C2H4/C2H6 and C2H2/C2H4. At this time, the two determining processes may be performed in parallel. Accordingly, the internal fault may be determined by using one or more xy-plane views selected from the fifth and sixth xy-plane views.

Here, the oil-immersed transformer of which the internal default is known refers to the oil-immersed transformer, which has a failure (internal fault), among the oil-immersed transformers used in a field, and is used for inspecting a correlation between the content ratio by matching the content ratios of the dissolved gases corresponding to the internal fault in the state that the internal fault occurs. On the other hand, the oil-immersed transformer for the diagnosis refers to an oil-immersed transformer of which an internal fault is able to be diagnosed by using the xy-plane view.

FIGS. 2 to 5 are first to fourth plane views according to the first embodiment of the present invention.

FIGS. 2 to 5 shows the first to fourth xy-plane views on which the internal faults of the plurality of oil-immersed transformers, of which the type of the internal faults is already known, are indicated according to the composition ratios of the corresponding dissolved gases by defining the value of CH4/H2 and C2H2/C2H4, the value of C2H2/C2H4 and C2H4/C2H6, the value of C2H4/C2H6 and C2H4/CH4, and the value of C2H2/C2H4 and C2H4/C2H6 as an X axis and a Y axis. In the embodiment, for example, the content ratio of each dissolved gas for a failure (the type of the internal fault) is analyzed with respect to the plural oil-immersed transformers of which the internal faults occur in an operation of the oil-immersed transformers in a field.

Figure 2:
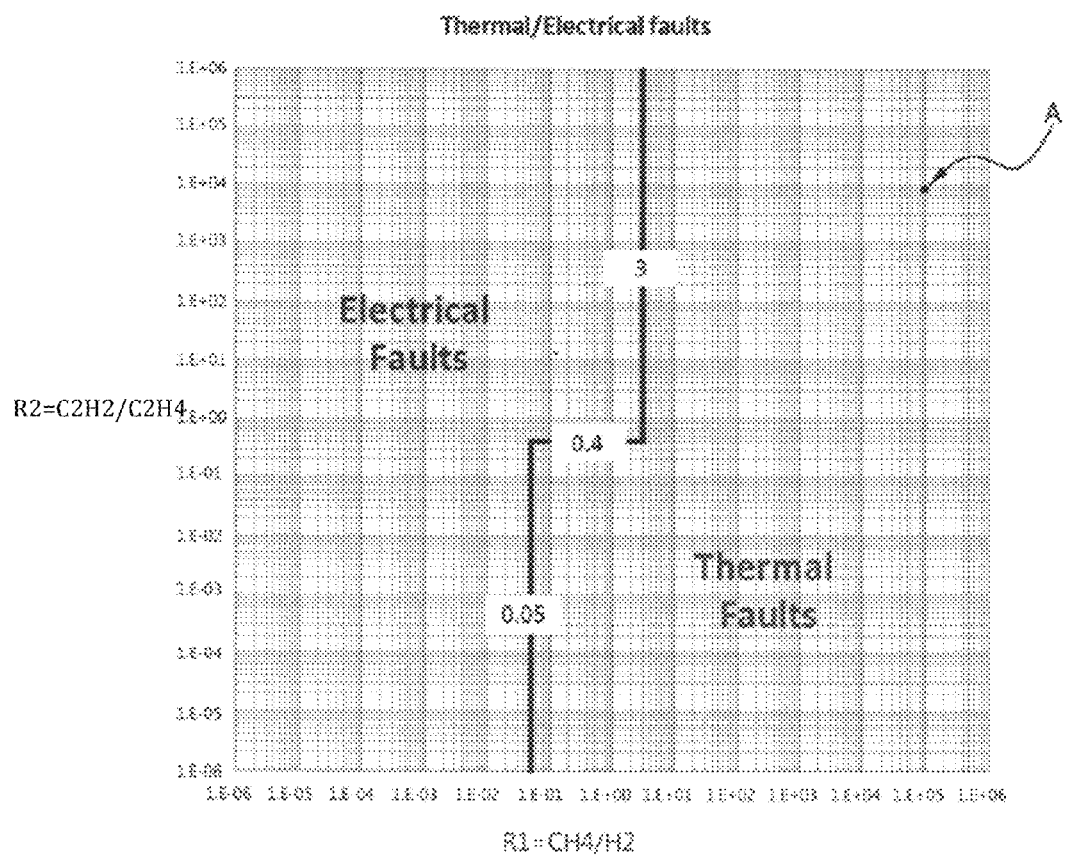
FIGS. 2 to 5 are first to fourth plane views according to the first embodiment of the present invention.

Particularly, in FIG. 2, CH4/H2 and C2H2/C2H4 are defined as the x-axis and the y-axis, and a range thereof is set to $1.0\times10^{-6} \sim 1.0\times10^{6}$. For example, a reference symbol A indicates a specific oil-immersed transformer in which CH4/H2 and C2H2/C2H4 are $1.0\times10^{5}$, and $1.0\times10^{4}$ respectively. The type of the internal fault indicates CH4/H2-C2H2/C2H4 of each of the plurality of oil-immersed transformers of which the type of the internal fault is already known, and is shown as in the first xy-plane view of FIG. 2. Further, the values indicated on the first xy-plane view of FIG. 2 are classified according to each of the types of the internal faults, so as to determine a fault region. At this time, the internal fault is classified into the electrical fault (E) and the thermal fault (E). The range of CH4/H2-C2H2/C2H4 according to each of the internal faults determined in the first xy-plane view according to the embodiment is indicated in Table 1 below.

Figure 3:
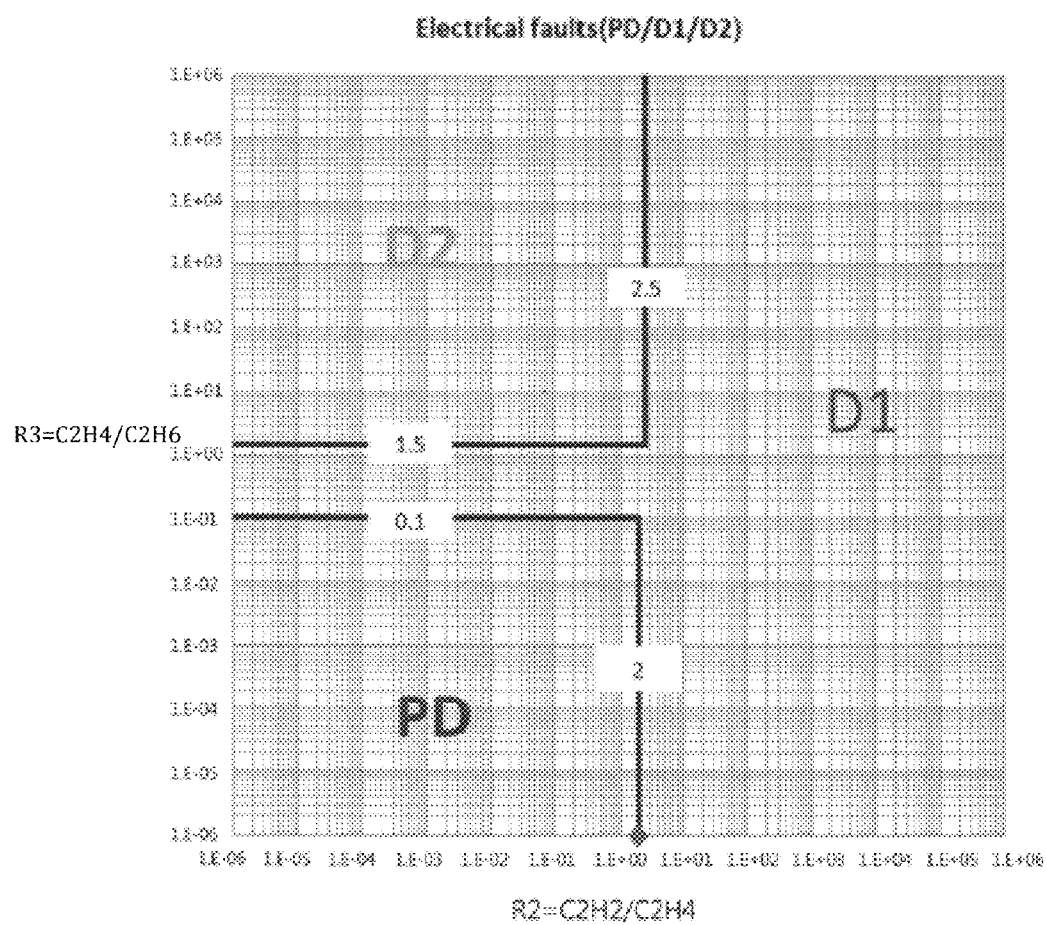
Figure 4:
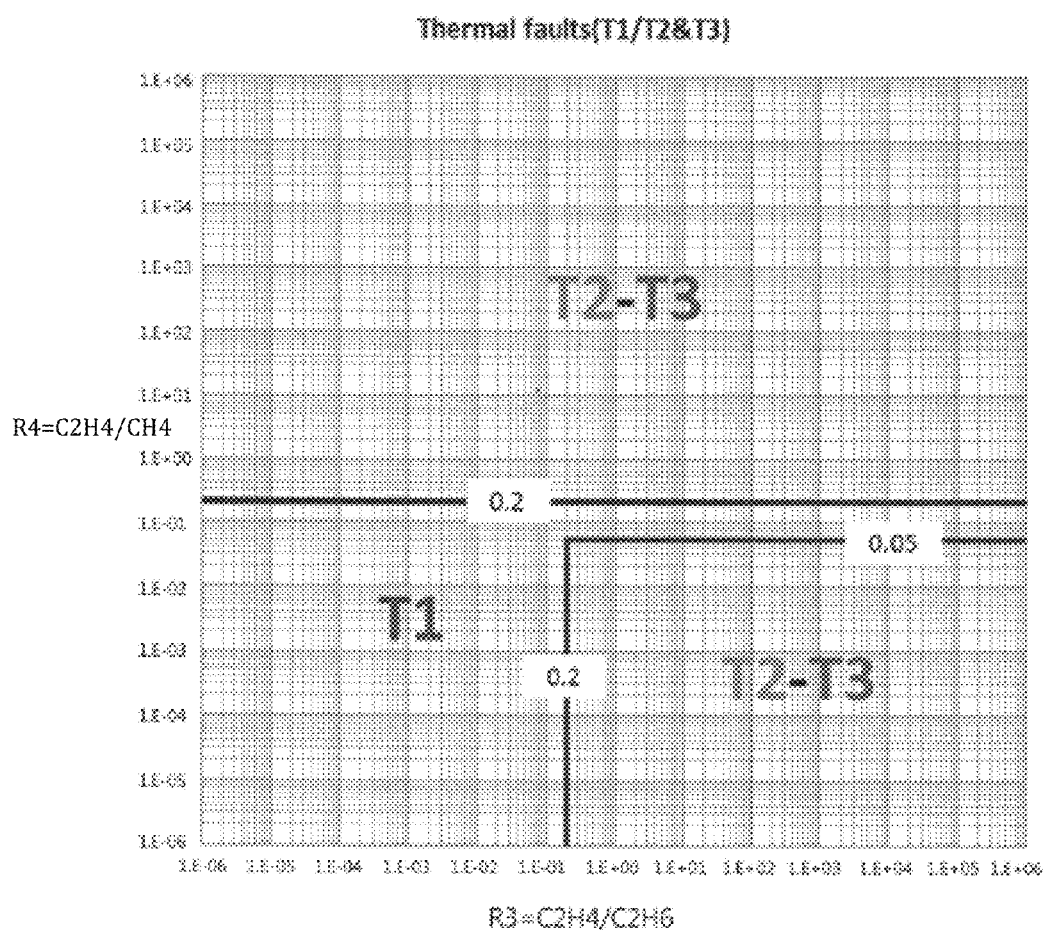
Figure 5:
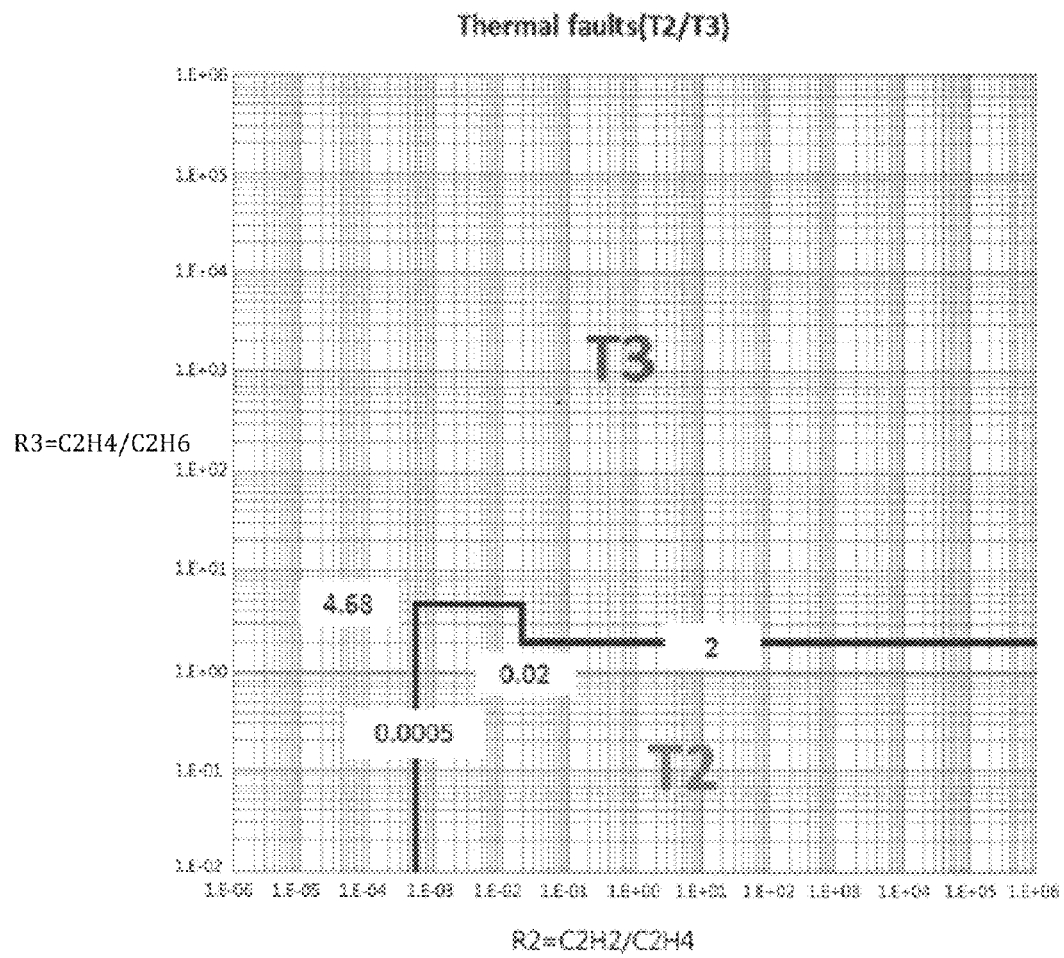

On the other hand, in FIG. 3, C2H2/C2H4 and C2H4/C2H6 are set as an x-axis and a y-axis, in FIG. 4, C2H4/C2H6 and C2H4/CH4 are set as an x-axis and a y-axis, and in FIG. 5, C2H2/C2H4 and C2H4/C2H6 are set as an x-axis and a y-axis. The range of the x- and y-axes are set to $1.0\times10^{-6} \sim 1.0\times10^{6}$. Further, in FIGS. 3 to 5, the type of the internal fault is classified by using the values indicated on the xy-plane views of FIGS. 2 to 4, so as to determine a fault region. The ranges of the composition ratios of each dissolved gas according to each internal fault determined in the second to fourth xy-planes are indicated in Tables 2, 3 and 4.

Firstly, on the second xy-plane view of FIG. 3, the partial discharge PD, the low energy discharge D1, and the high energy discharge D2 of the electrical fault E are determined.

TABLE 2

| Classification (Second X-Y plane) | Condition 1 | | Condition 2 | | Condition 3 | |
|---|---|---|---|---|---|---|
| | X | Y | X | Y | X | Y |
| PD | X ≤ 2 | Y ≤ 1 | | | | |
| D1 | X ≥ 2 | Y ≤ 1.5 | X ≤ 2 | 0.1 < Y ≤ 1.5 | X > 2.5 | Y > 1.5 |
| D2 | X ≤ 2.5 | Y > 1.5 | | | | |

Further, in the third xy-plane of FIG. 4, the first thermal fault (t<300° C.) (T1), the second thermal fault (300° C.<t<700° C.) (T2), or the third thermal fault (t>700° C.) (T3) is determined.

TABLE 3

| Classification (third X-Y plane) | Condition 1 | | Condition 2 | |
|---|---|---|---|---|
| | X | Y | X | Y |
| T1 | X ≤ 0.2 | Y ≤ 0.2 | X > 0.2 | 0.05 < Y ≤ 0.2 |
| T2&T3 | X > 0.2 | Y ≤ 0.05 | | Y > 0.2 |

Further, in the fourth xy-plane of FIG. 5, particularly, it is determined whether the internal fault is the second thermal fault (300° C.<t<700° C.) (T2) or the third thermal fault (t>700° C.).

TABLE 4

| Classification (Third X-Y plane) | Condition 1 | | Condition 2 | | Condition 3 | |
|---|---|---|---|---|---|---|
| | X | Y | X | Y | X | Y |
| T2 | X > 0.0005 | Y ≤ 2 | 0.0005 < X ≤ 0.02 | 2 < Y ≤ 4.68 | | |
| T3 | X ≤ 0.0005 | | 0.0005 < X ≤ 0.02 | Y > 4.68 | X > 0.02 | Y > |

As described above, the internal fault of the oil-immersed transformer for the diagnosis, of which the internal fault is able to be diagnosed, is determined by using the fault region for each internal fault, which is divided on the first to fourth xy-plane view. That is, the fault region corresponding to the first to fourth xy-plane views is determined by defining CH4/H2 and C2H2/C2H4, C2H2/C2H4 and C2H4/C2H6, C2H4/C2H6 and C2H4/CH4, and C2H2/C2H4 and C2H4/C2H6 as x and y coordinates, and the corresponding internal fault is determined from the fault region.

Figure 6:
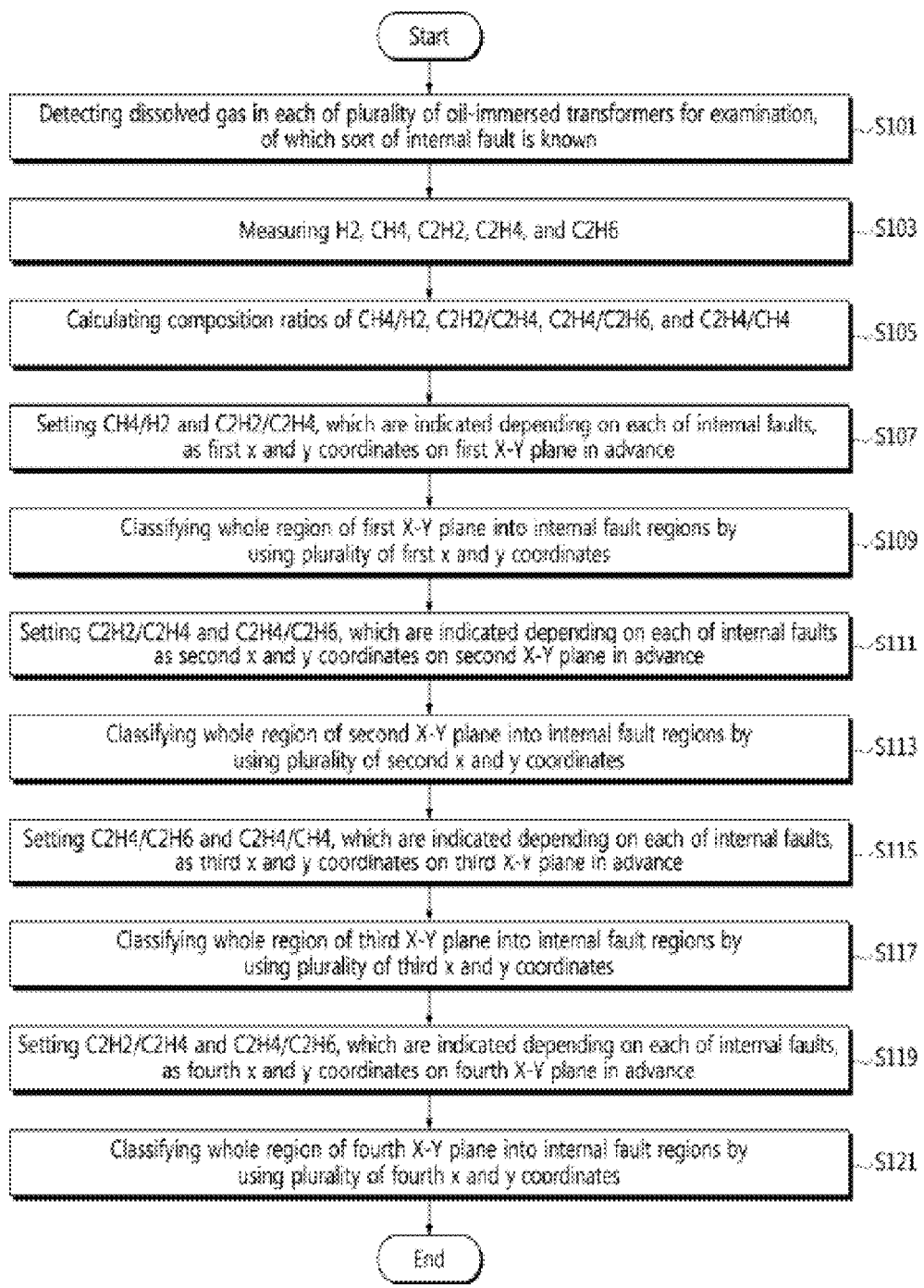
FIG. 6 is a flowchart illustrating a process of setting the first to fourth X-Y plane views according to the first embodiment of the present invention.

FIG. 6 is a flowchart illustrating a process of setting the first to fourth xy-plane views according to the first embodiment of the present invention.

Referring to FIG. 6, according to the first embodiment of the present invention, the dissolved gases, contained in the insulating oil in each of a plurality of oil-immersed transformers of which the type of the internal fault is already known, are detected in step S101. H2, CH4, C2H2, C2H4 and C2H6 are extracted from the dissolved gases which are detected as described above, and the quantities thereof are measured in step S103. The composition ratios of CH4/H2, C2H2/C2H4, C2H4/C2H6, and C2H4/C2H4 in the dissolved gases having five components, which are extracted as described above, are calculated in step S105. The first to fourth xy-plane views are set by using the plurality of composition ratios which are calculated as described above.

First, the process of setting the first xy-plane view will be described. The values of CH2/H2 and C2H2/C2H4, which are indicated depending on the types of the internal faults respectively in each oil-immersed transformer of which the types of the internal faults are already known, are set as first x and y coordinates on the first xy-plane in step S107, and a whole region of the first xy-plane is divided into an electrical fault (E) region and a thermal fault (T) region by using the plurality of first x and y coordinates which are set, in step S109.

Then, the values of C2H2/C2H4 and C2H4/C2H6, which are indicated depending on the type of the internal fault, are set as second x and y coordinates on the second xy-plane in step S111, and a whole region of the second X-Y plane is

TABLE 1

| Classification (first X-Y plane) | Condition 1 | | Condition 2 | |
|---|---|---|---|---|
| | X | Y | X | Y |
| E | X ≤ 0.05 | Y ≤ 0.4 | X ≤ 3 | Y > 0.4 |
| T | X > 0.05 | Y ≤ 0.4 | X > 3 | Y > 0.4 | divided into the partial discharge (PD) region, the low energy discharge (D1) region, and the high energy discharge (D2) region by using the plurality of second x and y coordinates which are set, in step S113.

Further, the values of C2H4/C2H6 and C2H4/CH4, which are indicated depending on the type of internal fault, are set as third x and y coordinates on the third xy-plane in step S115, and a whole region of the third xy-plane is divided into the first thermal fault (t<300° C.) (T1) region, the second thermal fault (300° C.<t<700° C.) (T3) region, or the third thermal fault (t>700° C.) (T3) region in step S117.

Continuously, the values of C2H4/C2H4 and C2H4/C2H6, which are indicated depending on the type of internal fault, are set as fourth x and y coordinates on the fourth xy-plane in step S119, and a whole region of the fourth xy-plane is divided into the second thermal fault (300° C.<t<700° C.) (T3) region and the third thermal fault (t>700° C.) (T3) region in step S121.

As described above, the first to fourth xy-plane views are used to acquire the composition ratios of the dissolved gases which are selected from five dissolved gases extracted from the plurality of oil-immersed transformers of which the type of the internal fault is already known, and to set the composition ratios as the x and y coordinates on the xy-plane, so as to classify each fault region. The first to fourth plane views are used to determine the internal fault of the oil-immersed transformer for the diagnosis, of which the internal fault is able to be diagnosed.

Figure 7:
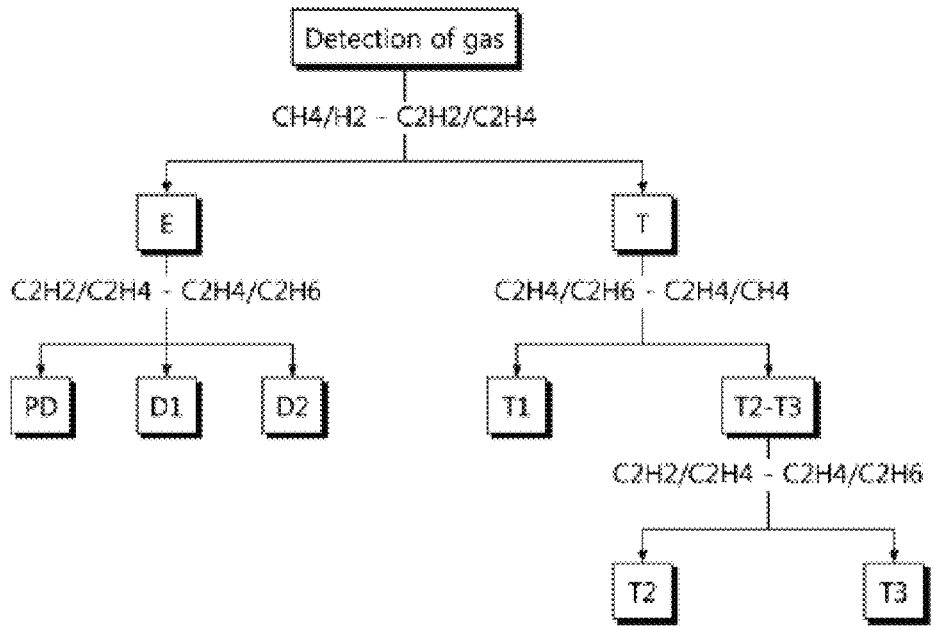
FIG. 7 is a schematic view illustrating a process of diagnosing an internal fault of an oil-immersed transformer according to the first embodiment of the present invention.

FIG. 7 is a schematic view illustrating a process of diagnosing an internal fault of an oil-immersed transformer according to the first embodiment of the present invention.

Referring to FIG. 7, in the process of diagnosing the internal fault of the oil-immersed transformer according to the first embodiment of the present invention, firstly, it is determined whether the internal fault of the oil-immersed transformer for the diagnosis, of which the internal fault is diagnosed, is the electrical fault (E) or the thermal fault (T) by using CH4/H2 and C2H2/C2H4.

As a result of the determination, if the internal fault is the electrical fault (E), it is determined whether the internal fault is the partial discharge (PD), the low energy discharge (D1), or the high energy discharge (D2), by using C2H2/C2H4 and C2H4/C2H6.

However, as a result of the determination, if the internal fault is the thermal fault (T), it is determined whether the internal fault is the first thermal fault (t<300° C.) (T1), the second thermal fault (300° C.<t<700° C.) (T2), or the third thermal fault (t>700° C.) (T3), by using C2H4/C2H6 and C2H4/CH4. Here, particularly, it is determined again whether the internal fault is the second thermal fault (300° C.<t<700° C.) (T2), or the third thermal fault (t>700° C.) (T3), by using C2H2/C2H4 and C2H4/C2H6.

Figure 8:
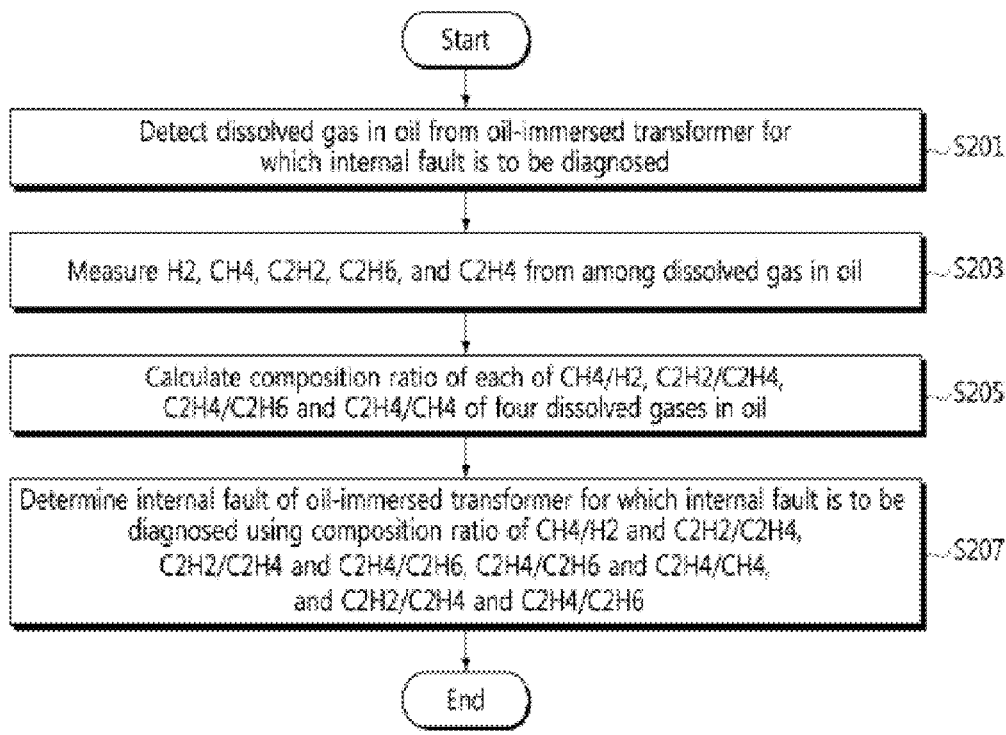
FIG. 8 is a flowchart illustrating a process of diagnosing the internal fault of an oil-immersed transformer through composition ratios of dissolved gases according to the second embodiment of the present invention.

FIG. 8 is a flowchart illustrating a process of diagnosing the internal fault of the oil-immersed transformer according to the first embodiment of the present invention.

Referring to FIG. 8, in the process of diagnosing the internal fault of the oil-immersed transformer according to the first embodiment of the present invention, the dissolved gases are detected from the oil-immersed transformer for the diagnosis of which the internal fault is able to be diagnosed, in step S201. H2, CH4, C2H2 and C2H4 are extracted from the dissolved gases which are detected as described above, and the quantities thereof are measured respectively in step S203. The composition ratios of CH4/H2, C2H2/C2H4, C2H4/C2H6, and C2H4/C2H4 in the dissolved gases having five components, which are extracted as described above, are calculated in step S205. The internal fault of the oil-immersed transformer for the diagnosis is determined by using CH4/H2 and C2H2/C2H4, C2H2/C2H4 and C2H4/C2H6, C2H4/C2H6 and C2H4/CH4, and C2H2/C2H4 and C2H4/C2H6 which are calculated, in step S207. Here, in step S207 of determining the internal fault, a region corresponding to the value of CH4/H2 and C2H2/C2H4 is determined in a fault region divided in the first xy-plane, and the electrical fault (E) and the thermal fault (T) are determined by using the determined fault region. Similarly, the regions corresponding to the values of C2H2/C2H4 and C2H4/C2H6 are determined in the fault region divided on the second xy-plane, and it is determined whether the internal fault is the partial discharge (PD), the low energy discharge (D1), and the high energy discharge (D2) of the electrical fault, by using the determined fault region. Further, the regions corresponding to the values of C2H4/C2H6 and C2H4/CH4 are determined in the fault region divided on the third xy-plane, and it is determined whether the internal fault is the first thermal fault (t<300° C.) (T1), the second thermal fault (300° C.<t<700° C.) (T2), or the third thermal fault (t>700° C.) (T3), by using the determined fault region. Further, the regions corresponding to the values of C2H2/C2H4 and C2H4/C2H6 are determined in the fault region divided on the fourth xy-plane, and it is determined whether the internal fault is the second thermal fault (300° C.<t<700° C.) (T2), or the third thermal fault (t>700° C.) (T3), by using the determined fault region.

As shown in FIGS. 2 to 8, in the first embodiment of the present invention, the internal fault of the oil-immersed transformer is accurately diagnosed by using the composition ratios of the dissolved gases generated when the internal fault of the oil-immersed transformer occurs.

Hereinafter, the method of diagnosing the internal fault of the oil-immersed transformer according to the second embodiment of the present invention will be described in detail.

Figure 9:
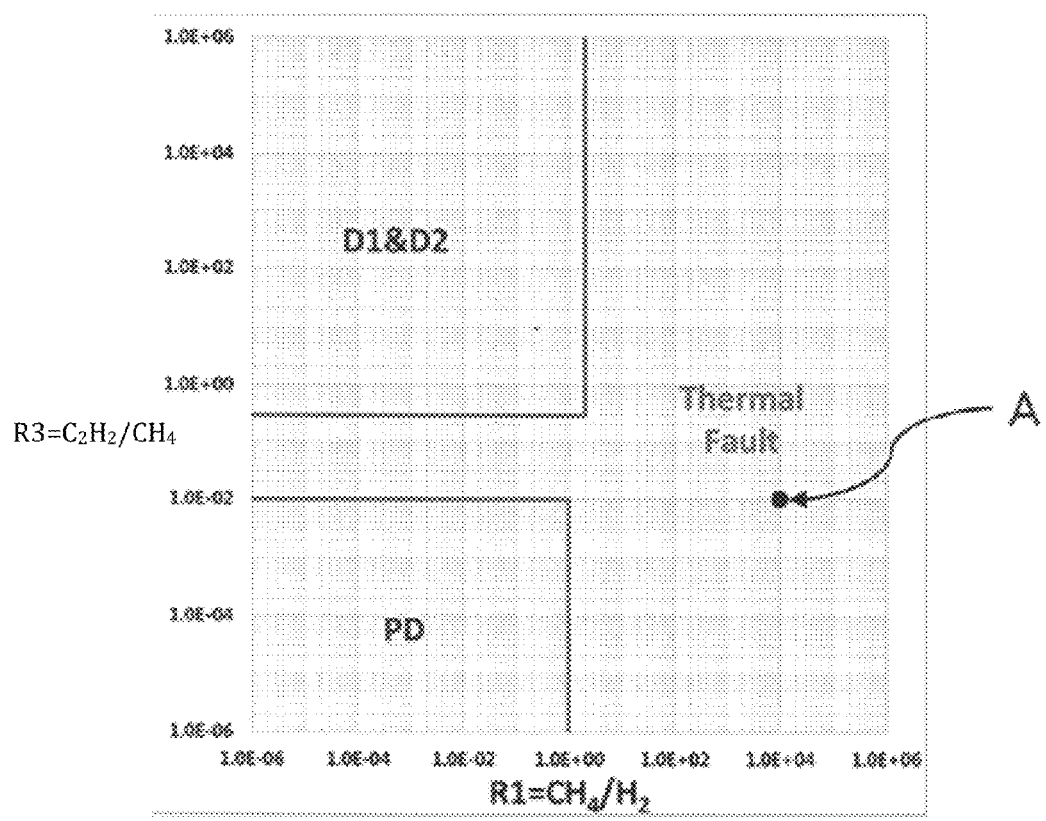
FIGS. 9 and 10 are fifth and sixth xy-plane views according to the second embodiment of the present invention.
Figure 10:
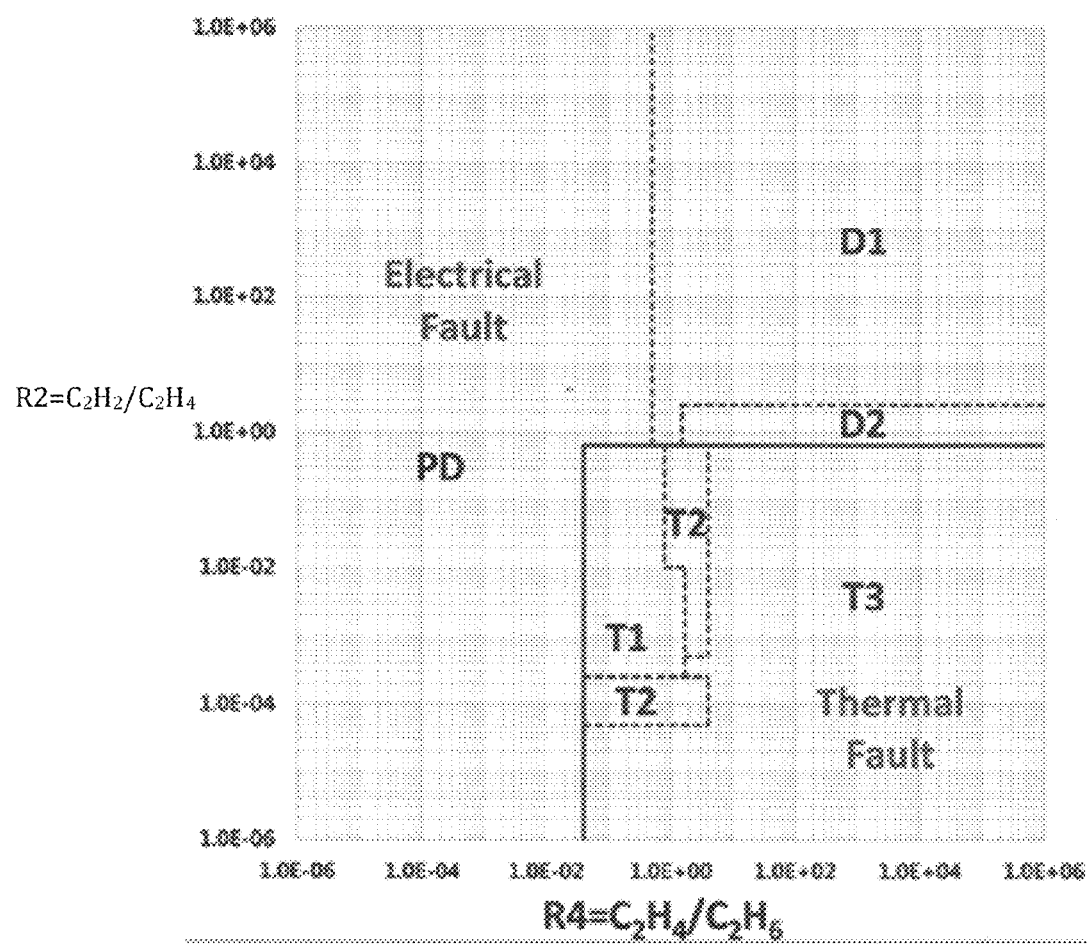

FIGS. 9 and 10 are fifth and sixth xy-plane views according to the second embodiment of the present invention.

FIGS. 9 and 10 show the internal fault according to the composition ratios of the corresponding dissolved gases on the fifth and sixth xy-plane views, in which CH4/H2 and C2H2/CH4, and C2H4/C2H6 and C2H2/C2H4 are defined as an x-axis and a y-axis respectively with respect to the plurality of the oil-immersed transformers, of which the type of the internal fault is known. In the embodiment, for example, the composition ratio of the corresponding dissolved gas for a failure (the type of the internal fault) is analyzed with respect to the plural oil-immersed transformers of which the internal faults occur in an operation of the oil-immersed transformers in a field.

Particularly, in FIG. 9, CH4/H2 and C2H2/C2H4 are defined as the x-axis and the y-axis, and a range thereof is set to 1.0×10-6~1.0×106. For example, a reference symbol A indicates a specific oil-immersed transformer in which CH4/H2 is 1.0×104, and C2H2/CH4 is 1.0×10-2. As described above, CH4/H2-C2H2/CH4 of each of the plurality of oil-immersed transformers is shown in the fifth xy-plane view of FIG. 9. Further, the values indicated on the fifth xy-plane view of FIG. 9 are classified according to each of the types of the internal faults, so as to determine a fault region. At this time, the classified internal fault is the thermal fault (T), or the partial discharge (PD) or the energy discharge (D1 or D2) of the electrical fault (E). The range of CH4/H2-C2H2/C2H4 according to each of the internal faults determined in the fifth xy-plane view according to the embodiment is indicated in Table 5 below.

TABLE 5

| Classification (First X-Y plane) | Condition 1 X (CH4/H2) | Condition 2 Y (C2H2/CH4) |
|---|---|---|
| Thermal | 2 < X | 0.3 < Y |
|  |  | 0.01 < Y ≤ 0.3 |
|  | 1 < X | Y ≤ 0.01 |
| PD | X ≤ 1 | Y ≤ 0.01 |
| D1&D2 | X ≤ 2 | 0.3 < Y |

On the other hand, in FIG. 10, C2H4/C2H6 and C2H2/C2H4 are defined as an x-axis and a y-axis respectively, and the range thereof is set to 1.0×10-6~1.0×106. Further, the values indicated on the sixth xy-plane view of FIG. 10 are classified according to each of the types of the internal faults, so as to determine a fault region. The ranges of the composition ratios of the dissolved gases according to each internal fault determined in the sixth xy-plane view are indicated in Table 6. Through the sixth xy-plane of FIG. 10, it is determined whether the internal fault is the thermal fault, or the partial discharge (PD) or the energy discharge (D1 or D2) of the electrical fault (E).

TABLE 6

| Classification (Second X-Y plane) | Condition 1 X (C2H4/C2H6) | Condition 2 Y (C2H2/C2H4) |
|---|---|---|
| PD | X ≤ 0.04 |  |
|  | 0.04 < X ≤ 0.5 | 0.65 < Y |
| D1 | 0.5 < X ≤ 1.5 | 0.65 < Y |
|  | 1.5 < X | 2.5 < Y |
| D2 | 1.5 < X | 0.65 < Y ≤ 2.5 |
| T1 | 0.04 < X ≤ 1.7 | 0.00025 < Y ≤ 0.01 |
|  | 0.04 < X ≤ 0.8 | 0.01 < Y ≤ 0.65 |
| T2 | 1.7 < X ≤ 4 | 0.0005 < Y ≤ 0.01 |
|  | 0.8 < X ≤ 4 | 0.01 < Y ≤ 0.65 |
|  | 0.04 < X ≤ 4 | 0.00005 < Y ≤ 0.00025 |
| T3 | 0.04 < X ≤ 4 | Y ≤ 0.00005 |
|  | 1.7 < X ≤ 4 | 0.00025 < Y ≤ 0.0005 |
|  | 4 < X | Y ≤ 0.65 |

As described above, the internal fault of the oil-immersed transformer for the diagnosis, of which the internal fault is able to be diagnosed, is determined by using the fault region for each internal fault, which is divided on the fifth to sixth xy-plane view. That is, the fault regions corresponding to the fifth and sixth xy-plane views are determined by using the CH4/H2 and C2H2/CH4, and C2H4/C2H6 and C2H2/C2H4, which are calculated in the oil-immersed transformer for the diagnosis, as the x and y coordinates, and the internal fault corresponding to the fault region is determined.

Figure 11:
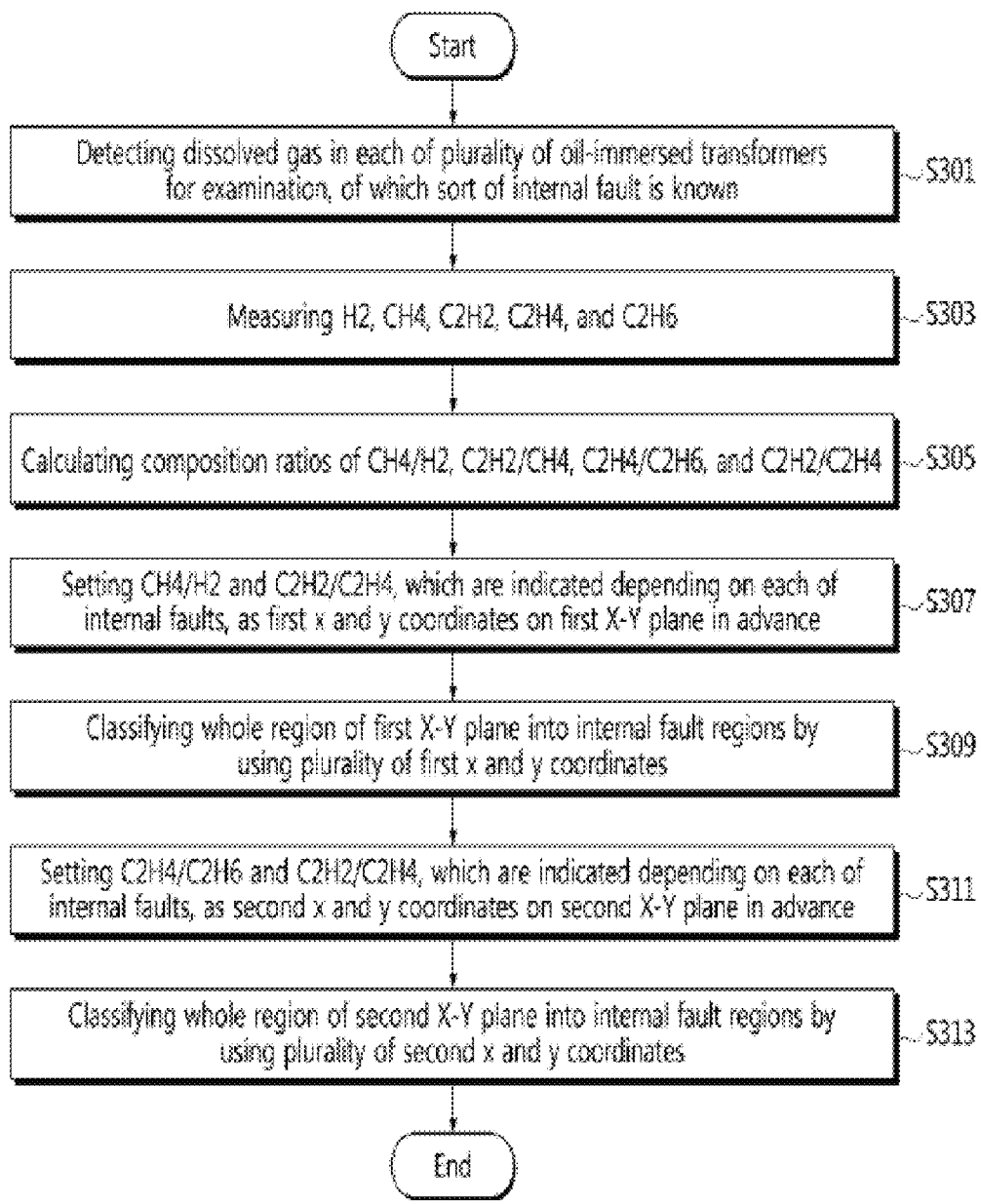
FIG. 11 is a flowchart illustrating a process of setting the fifth and sixth xy-plane views according to the second embodiment of the present invention.

FIG. 11 is a flowchart illustrating a process of setting the fifth and sixth xy-plane views according to the second embodiment of the present invention.

Referring to FIG. 11, in the second embodiment according to the present invention, the dissolved gases, which are contained in the insulating oil in each of the plurality of oil-immersed transformers of which the internal faults are already known, are detected in step S301. H2, CH4, C2H2, C2H4 and C2H6 are extracted from the dissolved gases which are detected as described above, and the quantities thereof are measured in step S303. The composition ratios of CH4/H2, C2H2/CH4, C2H4/C2H6, and C2H2/C2H4 in the dissolved gases having five components, which are extracted as described above, are calculated in step S305. The fifth to sixth xy-plane views are set by using the plurality of composition ratios which are calculated as described above.

First, the process of setting the fifth xy-plane view will be described. The values of CH4/H2 and C2H2/CH4, which are indicated depending on the types of the internal faults respectively in each oil-immersed transformer of which the types of the internal faults are already known, are set as fifth x and y coordinates on the fifth xy-plane in step S307, and a whole region of the fifth xy-plane is divided into the thermal fault (T) region, and the partial discharge (PD) region, and the energy discharge (D1 or D2) region of the electrical fault (T) region by using the plurality of fifth x and y coordinates which are set, in step S309.

Then, the values of C2H4/C2H6 and C2H2/C2H4 which are indicated depending on the type of the internal faults are set as the sixth x and y coordinates on the sixth xy-plane in step S311, and a whole region of the sixth xy-plane is classified by using the plurality of sixth x and y coordinates into the partial discharge (PD) region, the low energy (D1) region, and the high energy discharge (D2) region of the electrical fault (E), and the first thermal fault (t<300° C.) (T1) region, the second thermal fault (300° C.<t<700° C.) (T2) region, and the third thermal fault (t>700° C.) (T3) region of the thermal fault (T).

As described above, the fifth to sixth xy-plane views are used to acquire the composition ratios of the dissolved gases which are selected from five dissolved gases extracted from the plurality of oil-immersed transformers of which the type of the internal fault is already known, and to set the composition ratios as the x and y coordinates on the xy-plane respectively, so as to classify each fault region. The fifth and sixth plane views are used to determine the internal fault of the oil-immersed transformer for the diagnosis, of which the internal fault is able to be diagnosed.

Figure 12:
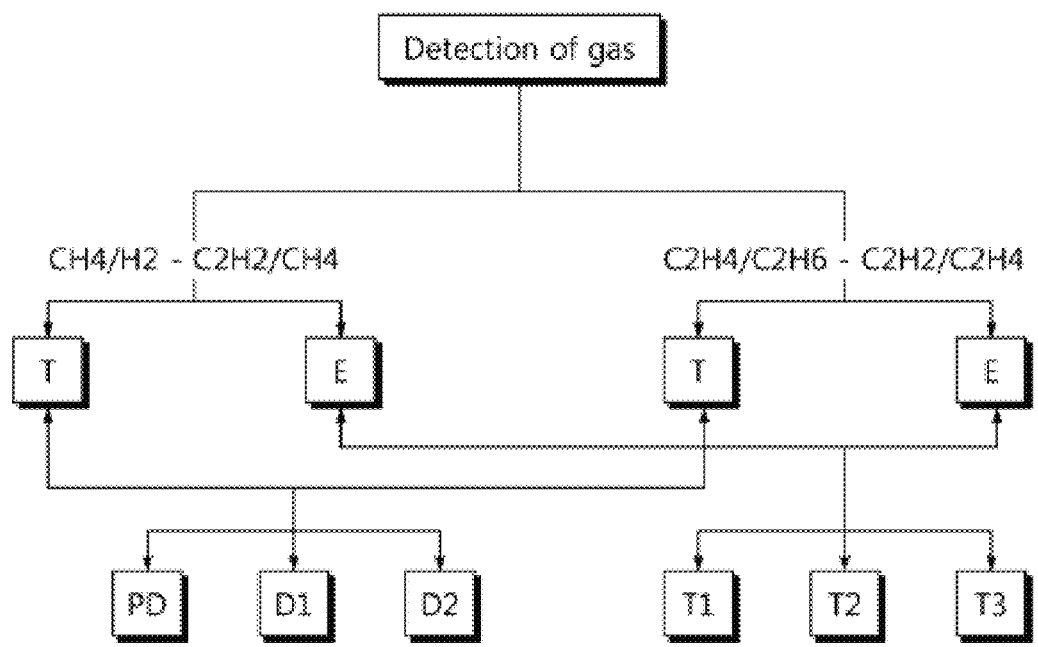
FIG. 12 is a schematic view illustrating a process of diagnosing an internal fault of the oil-immersed transformer according to the second embodiment of the present invention.

FIG. 12 is a schematic view illustrating a process of diagnosing an internal fault of the oil-immersed transformer according to the second embodiment of the present invention.

Referring to FIG. 12, in the process of diagnosing the internal fault of the oil-immersed transformer according to the second embodiment of the present invention, with respect to the oil-immersed transformer for the diagnosis of which the internal fault is able to be diagnosed, it is determined whether the internal fault is the partial discharge (PD), the low energy discharge (D1), or the high energy discharge (D2), or whether the internal fault is the first thermal fault (t<300° C.) (T1), the second thermal fault (t>300° C.) (T2), or the third thermal fault (t>300° C.) (T3), by using one of CH4/H2 and C2H2/CH4, or alternatively, one of C2H4/C2H6 and C2H2/C2H4.

Figure 13:
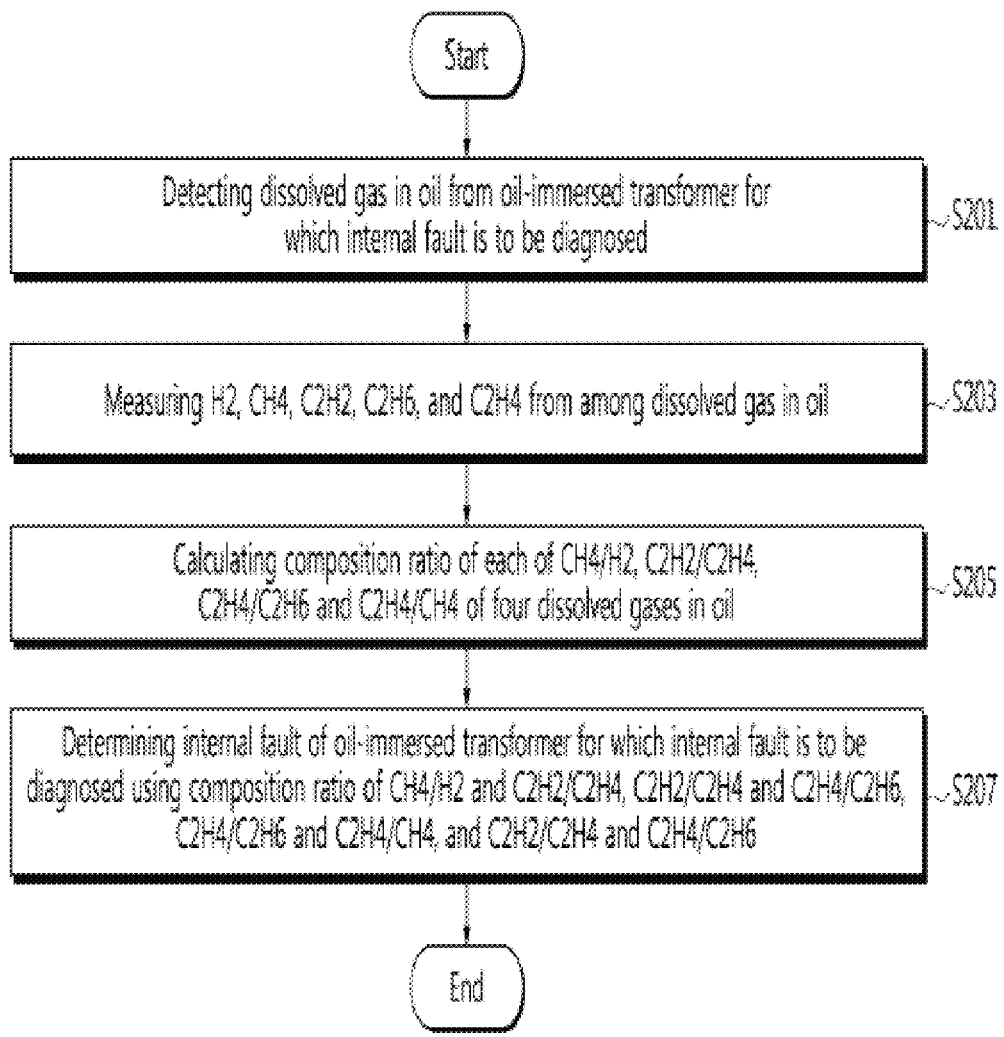
FIG. 13 is a flowchart illustrating a process of diagnosing the internal fault of an oil-immersed transformer through composition ratios of dissolved gases according to the second embodiment of the present invention.

FIG. 13 is a flowchart illustrating a process of diagnosing the internal fault of the oil-immersed transformer through composition ratios of dissolved gases according to the second embodiment of the present invention.

Referring to FIG. 13, in the process of diagnosing the internal fault of the oil-immersed transformer according to the second embodiment of the present invention, the dissolved gases are detected from the oil-immersed transformer for the diagnosis, of which the internal faults are able to be diagnosed in step S401. H2, CH4, C2H2, C2H4 and C2H6 are extracted from the dissolved gases which are detected as described above, and the quantities thereof are measured in step S403. The composition ratios of CH4/H2, C2H2/CH4, C2H4/C2H6, and C2H2/C2H4 in the dissolved gases having five components, which are extracted as described above, are calculated in step S405. Then, the internal fault of the corresponding oil-immersed transformer for the diagnosis is determined by using CH4/H2, C2H2/CH4, C2H4/C2H6, and C2H2/C2H4 which are calculated in step S407. Here, in step S407 of determining the internal fault, the region corresponding to the value of CH4/H2 and C2H2/CH4 is determined in the fault region divided on the fifth xy-plane, and it is determined whether the internal fault is the thermal fault (T), or the partial discharge (PD) or the energy discharge (D1 or D2) of the electrical fault (E) by using the determined region.

Similarly, the region corresponding to the value of C2H4/C2H6 and C2H2/C2H4 is determined in the fault region divided on the sixth xy-plane, and it is determined whether the internal fault is the partial discharge (PD), the low energy discharge (D1), or the high energy discharge (D2) of the electrical fault (E), or the first thermal fault (t<300° C.) (T1), the second thermal fault (300° C.<t<700° C.), or the third thermal fault (t>700° C.) (T3), by using the determined region. At this time, the determination of the internal fault using the first to fourth xy-plane views may be performed in parallel. Accordingly, the internal fault may be determined by using one or more xy-plane view selected from the first to fourth xy-plane views.

Although the present invention has been described in detail through the exemplary embodiments, it will be known that the present invention is not limited to the contents of the embodiments. It is obvious to those skilled in the art to which the present invention pertains that the present invention may be modified and varied within the scope of the accompanying claims although the variation and modification are described in the embodiments, and the variation and the modification belong to the technical scope of the present invention. Therefore, the technical scope of the present invention should be defined by the technical spirit of the accompanying claims.

INDUSTRIAL APPLICABILITY

The oil-immersed transformer is electric equipment for increasing or decreasing a supplied voltage, and plays an important role in the electric power supplying system. When the internal fault occurs in the oil-immersed transformer, it may cause a failure in the supply of the electric power. According to it is important to detect the internal fault, thereby preventing an electrical accident.

In these terms, since the present invention can precisely diagnose the internal fault by extracting and analyzing the dissolved gases contained in the insulating oil in the oil-immersed transformer, the present invention may be efficiently used in the transformer substation, the electric power company, and the like, to which it is applied, as well as in manufacturing the oil-immersed transformer.

The invention claimed is:

1. A method for diagnosing an internal fault of an oil-immersed transformer by extracting and analyzing dissolved gases from the oil-immersed transformer of which the internal fault is able to be diagnosed, the method comprising:
a first step of presetting ratio of CH4/H2 and C2H2/C2H4, which are indicated depending on the types of the internal faults respectively in each oil-immersed transformer of which the types of the internal faults are already known, as first x and y coordinates on a first xy-plane, presetting ratio of C2H2 /C2H4 and C2H4 /C2H6, which are indicated depending on the types of the internal faults respectively in the oil-immersed transformer, as second x and y coordinates on a second xy-plane, and classifying the first and second xy-planes into fault region corresponding to the type of the internal faults by using the first and second x and y coordinates which are preset on the first and second xy-planes;
a second step of calculating composition ratios of CH4/H2, C2H2/C2H4, C2H4/C2H6, and C2H4/CH4 among the dissolved gases which are extracted from the oil-immersed transformer of which the internal fault is able to be diagnosed;
a third step of determining whether the internal fault is an electrical fault (E) or a thermal fault (T) by making the calculated ratios of CH4/H2 and C2H2/C2H4 to correspond to the fault region corresponding to the type of the internal faults on the first xy-plane which is classified at the first step; and
a fourth step of determining whether the internal fault is a partial discharge (PD), a low energy discharge (D1), or a high energy discharge (D2) by making the calculated ratios of C2H2/C2H4 and C2H4/C2H6 to the fault region corresponding to the type of the internal faults on the second xy-plane which is classified at the first step, if the internal fault is the electrical fault (E) as a result of the determination in the third step.

2. The method as claimed in claim 1, wherein the third step comprises:
presetting CH4/H2 and C2H2/C2H4, which are indicated depending on each of the electric fault and the thermal fault in each of a plurality of oil-immersed transformers of which a type of the internal fault is known, as the first x and y coordinates on the first xy-plane; and
classifying a whole region of the first xy-plane into the electric fault (E) and the thermal fault (T) by using the plurality of the first x and y coordinates which are set,
wherein it is determined whether the internal fault is the electric fault (T) or the thermal fault (E) by using a region corresponding to the plural coordinates for CH4/H2 and C2H2/C2H4 which are calculated in the second step.

3. The method as claimed in claim 1, wherein the fourth step comprises:
setting C2H2/C2H4 and C2H4/C2H6, which are indicated depending on each of the partial discharge (PD), the high energy discharge (D1), and the low energy discharge (D2) in each of a plurality of oil-immersed transformers in which the electric fault occurs, as x and y coordinates on a second xy-plane; and
classifying a whole region of the second xy-plane into the partial discharge (PD), the low energy discharge (D1), and the high energy discharge (D2) by using the plurality of x and y coordinates which are set,
wherein it is determined whether the internal fault is the partial discharge (PD), the low energy discharge (D1), or the high energy discharge (D2), by using the region corresponding to the plural coordinates for C2H2/C2H4 and C2H4/C2H6 which are calculated in the second step.

4. The method as claimed in claim 1, further comprising:
a fifth step of determining whether the internal fault is the first thermal fault (t<300° C.) (T1), the second thermal fault (300° C.<t<700° C.)(T2), or the third thermal fault (t>700° C.) (T3), by using C2H4/C2H6 and C2H4/CH4 which are calculated, if the internal fault is the thermal fault (T) as a result of the determination in the third step; and
a sixth step of determining whether the internal fault is the second thermal fault (300° C.<t<700° C.)(T2) or the third thermal fault (t>700° C.)(T3), by using C2H2/C2H4 and C2H4/C2H6, if the internal fault is the second thermal fault (300° C.<t<700° C.)(T2) or the third thermal fault (t>700° C.)(T3) as a result of the determination in the fifth step.

5. The method as claimed in claim 4, wherein the fifth step comprises:
presetting C2H4/C2H6 and C2H4/CH4, which are indicated depending on the first thermal fault (t<300° C.), the second thermal fault (300° C.<t<700° C.)(T2), or the third thermal fault (t>700° C.)(T3) in each of the plurality of oil-immersed transformers of which the thermal fault occurs, as third x and y coordinates on a third xy-plane; and
classifying a whole region of the third xy-plane a first thermal region (T1), a second thermal fault, or a third thermal fault by using the third x and y coordinates which are set,
wherein it is determined whether the internal fault is the first thermal fault (T1), the second thermal fault, or the third thermal fault, by using a region corresponding to the plural coordinates for C2H4/C2H6 and C2H4/CH4 which are calculated in the second step.

6. The method as claimed in claim 5, wherein the sixth step comprises:
presetting C2H4/C2H4 and C2H4/C2H6, which are indicated depending on the second thermal fault (300° C.<t<700° C.)(T2) and the third thermal fault (t>700° C.)(T3) in each of the plurality of oil-immersed transformers of which a type of the internal faults is known, as fourth x and y coordinates on the fourth xy-plane; and
classifying a whole region of the fourth xy-plane into the second thermal fault (T2) region and the third thermal fault (T3) region by using the fourth x and y coordinates which are set,
wherein it is determined whether the internal fault is the second thermal fault or the third thermal fault, by using a region corresponding to the plural coordinates for C2H2/C2H4 and C2H4/C2H6 which are calculated in the second step.

7. A method of diagnosing an internal fault of an oil-immersed transformer through a composition ratio of a dissolved gas in oil, the method comprising:
a first step of calculating composition ratios of CH4/H2, C2H2/C2H4, C2H4/C2H6, and C2H4/CH4 of dissolved gases after extracting the dissolved gases from each of a plurality of oil-immersed transformers of which the internal fault is known;
a second step of classifying a whole region of the first xy-plane into an electrical fault (E) and a thermal fault (T) by using a plurality of x and y coordinates after setting CH4/H2 and C2H2/C2H4, which are indicated depending on each of the electrical fault (E) and the thermal fault (T) among the internal faults, as the x and y coordinates on the first xy-plane;
a third step of classifying a whole region of a second xy-plane into a partial discharge (PD) region, a low energy discharge (D1) region, and a high energy discharge (D2) region by using the plural x and y coordinates after setting C2H2/C2H4 and C2H4/C2H6, which are indicated depending on each of a partial discharge (PD), a low energy discharge (D1), and a high energy discharge (D2) among the internal faults, as the x and y coordinates on the second xy-plane;
a fourth step of classifying a whole region of a third xy-plane into a first thermal fault (T1) region, a second thermal fault (T2) region, and a third thermal fault (T3) region after setting C2H4/C2H6 and C2H4/CH4, which are indicated depending on each of a first thermal fault (t<300° C.)(T1), a second thermal fault (300° C.<t<700° C.)(T3), and a third thermal fault (t>700° C.)(T3) of the thermal fault (T), as the x and y coordinates on the third xy-plane;
a fifth step of classifying a whole region of a fourth xy-plane into the second thermal fault (T2) region and the third thermal fault (T3) region by using a plurality of x and y coordinates after setting C2H2/C2H4 and C2H4/C2H6, which are indicated depending on each of the second thermal fault (300° C.<t<700° C.)(T3) and the third thermal fault (t>700° C.)(T3), as the x and y coordinates on the third xy-plane respectively;
a sixth step of calculating composition ratios of CH4/H2, C2H2/C2H4, C2H4/C2H6, and C2H4/CH4 among the dissolved gases which are extracted from the oil-immersed transformer for diagnosis, of which the internal fault is able to be diagnosed; and
a seventh step of determining a region, which corresponds to the x and y coordinates of two selected from CH4/H2, C2H2/C2H4, C2H4/C2H6, and C2H4/CH4 which are calculated, on the first to fourth xy-planes, so as to determine a type of the internal fault of the oil-immersed transformer to be diagnosed, by using the determined region.

8. The method as claimed in claim 7, wherein the seventh step comprises:
determining a region, which corresponds to plural coordinates for CH4/H2 and C2H2/C2H4 which are calculated in the sixth step, on the first xy-plane, so as to determine whether the internal fault is the electric fault (E) or the thermal fault (T) by using the determined region.

9. The method as claimed in claim 8, wherein the seventh step comprises:
determining a region, which corresponds to plural coordinates for C2H2/C2H4 and C2H4/C2H6 calculated in the sixth step, on the second xy-plane if it is determined that the internal fault is the electrical fault (E), so as to determine whether the electrical fault is a partial discharge (PD), a low energy discharge (D1), or a high energy discharge (D2), by using the determined region.

10. The method as claimed in claim 8, wherein the seventh step comprises:
determining a region, which corresponds to plural coordinates for C2H4/C2H6 and C2H4/CH4 calculated in the sixth step, is determined on the third xy-plane if it is determined that the internal fault is the thermal fault (T), so as to determine whether the thermal fault (T) is a first thermal fault (t<300° C.)(T1), a second thermal fault (300° C.<t<700° C.)(T2), or a third thermal fault (t>700° C.)(T3), by using the determined region.

11. The method as claimed in claim 10, wherein a region, which corresponds to the x and y coordinate for C2H2/C2H4 and C2H4/C2H6 calculated in the sixth step, on the fourth xy-plane if it is determined that the thermal fault is the second thermal fault (300° C.<t<700° C.)(T2) or the third thermal fault (t>700° C.)(T3), so as to determine whether the thermal fault is the second thermal fault (300° C.<t<700° C.)(T2) or the third thermal fault (t>700° C.)(T3) by using the determined region.

12. The method as claimed in claim 7, wherein the electrical fault region of the whole region of the first xy-plane simultaneously satisfies a condition of CH4/H2<0.5 and C2H2/C2H4>0.4, and a condition of CH4/H2<3 and C2H2/C2H4>0.4, while the thermal fault region simultaneously satisfies a condition of CH4/H2>0.5 and C2H2/C2H4≤0.4, and a condition of CH4/H2>3 and C2H2/C2H4>0.4.

13. The method as claimed in claim 7, wherein the partial discharge (PD) region of the whole region of the second xy-plane satisfies a condition of C2H2/C2H4≤2 and C2H4/C2H6≤0.1, the low energy discharge (D1) region simultaneously satisfies a condition of C2H2/C2H4>2 and C2H4/C2H6≤1.5, a condition of C2H2/C2H4≤2 and 0.1<C2H4/C2H6≤1.5, and a condition of C2H2/C2H4>2.5 and C2H4/C2H6>1.5, and the high energy discharge (D2) region satisfies a condition of C2H2/C2H4≤2.5 and C2H4/C2H6>1.5.

14. The method as claimed in claim 7, wherein the first thermal fault (t<300° C.)(T1) region of the whole region of the third xy-plane simultaneously satisfies a condition of C2H4/C2H6≤0.2 and C2H4/CH4≤0.2, and a condition of C2H4/C2H6>0.2 and 0.05<C2H4/CH4≤0.2, and the second thermal fault (300° C.<t<700° C.)(T2) or the third thermal fault (t>700° C.) regions simultaneously satisfy a condition of C2H4/C2H6>0.2 and C2H4/CH4≤0.05 and a condition of C2H4/CH4>0.2.

15. The method as claimed in claim 7, wherein in the whole region of the fourth xy-plane, the second thermal fault (300° C.<t<700° C.)(T2) region simultaneously satisfies a condition of C2H2/C2H4>0.0005 and C2H4/C2H6≤2, and a condition of 0.0005<C2H2/C2H4≤0.02 and 2<C2H4/C2H6≤4.68, and the third thermal fault (t>700° C.)(T3) region simultaneously satisfies a condition of C2H2/C2H4≤0.0005, a condition of 0.0005<C2H2/C2H4≤0.02 and C2H4/C2H6>4.68, and a condition of C2H2/C2H4>0.02 and C2H4/C2H6>2.

16. A method of diagnosing an internal fault of an oil-immersed transformer by extracting and analyzing dissolved gases from the oil-immersed transformer of which the internal fault is able to be diagnosed, the method comprising:
  a first step of presetting CH4/H2 and C2H2/CH4, which are indicated depending on the types of the internal faults respectively in each oil-immersed transformer of which the types of the internal faults are already known, as fifth x and y coordinates on a fifth xy-plane, and classifying the fifth xy-plane into fault region corresponding to the type of the internal faults by using the fifth x and y coordinate which are preset on the fifth xy-plane;
  a second step of calculating CH4/H2 and C2H2/CH4 in the dissolved gases which are extracted from the oil-immersed transformer of which the internal fault is able to be diagnosed; and
  a third step of making the calculated CH4/H2 and C2H2/CH4 to correspond to the internal fault region corresponding to the type of the internal faults on the first xy-plane which is classified at the first step, so as to determine whether the internal fault is a thermal fault (T), or a partial discharge (PD) or an energy discharge (D1 or D2) of an electrical fault (E).

17. The method as claimed in claim 16, wherein the third step comprises:
  presetting CH4/H2 and C2H2/CH4, which are indicated depending on the thermal fault (T), or each of the partial discharge (PD) and the energy discharge (D1 or D2) of the electric fault (E) in each of a plurality of oil-immersed transformers of which the type of internal fault is known, as the fifth x and y coordinates on the fifth xy-plane in advance; and
  classifying a whole region of the fifth xy-plane into a thermal fault (T) region, and the partial discharge (PD) region and the energy discharge (D1 or D2) region of the electric fault (E),
  wherein it is determined whether the electric fault (E) is the partial discharge (PD) or the energy discharge (D1 or D2) by using a region corresponding to the plural coordinates for CH4/H2 and C2H2/C2H4 which are calculated in the first step second step.

18. A method of diagnosing an internal fault of an oil-immersed transformer by extracting and analyzing dissolved gases from the oil-immersed transformer of which the internal fault is able to be diagnosed, the method comprising:
  a first step of presetting C2H4/C2H6 and C2H2/C2H4, which are indicated depending on the types of the internal faults respectively in each oil-immersed transformer of which the types of the internal faults are already known, as sixth x and y coordinates on a sixth xy-plane, and classifying the sixth xy-plane into fault region corresponding to the type of the internal faults by using the sixth x and y coordinate which are preset on the sixth xy-plane;
  a second step of calculating C2H4/C2H6 and C2H2/C2H4 in the extracted and dissolved gases which are extracted from the oil-immersed transformer of which the internal fault is able to be diagnosed; and
  a third step of making the calculated C2H4/C2H6 and C2H2/C2H4 to correspond to the internal fault region corresponding to the type of the internal faults on the sixth xy-plane which is classified at the first step, so as to determine whether the internal fault is a partial discharge (PD), a low energy discharge (D1), or a high energy discharge (D2) of an electric fault (E), or a first thermal fault (t<300° C.)(T1), a second thermal fault (300° C.<t<700° C.) (T2), or a third thermal fault (t>700° C.)(T3).

19. The method as claimed in claim 18, wherein the third step comprises:
  setting C2H4/C2H6 and C2H2/C2H4, which are indicated depending on each of the partial discharge (PD), the low energy discharge (D1), and the high energy discharge (D2) of the electric fault (E), and the first thermal default (t<300° C.)(T1), the second thermal default (300° C.<t<700° C.)(T2), and the third thermal default (t>700° C.)(T3) in each of a plurality of oil-immersed transformers of which a type of internal faults is known, as the sixth x and y coordinates on a sixth xy-plane; and
  classifying a whole region of the sixth xy-plane into a partial discharge (PD) region, a low energy discharge (D2) region, a high energy discharge (D3) region, a first thermal fault (T1) region, a second thermal fault (T2) region, a third thermal fault (T3) region,
  wherein it is determined whether the internal fault is the partial discharge (PD), the low energy discharge (D2), the high energy discharge (D3), the first thermal fault (T1), the second thermal fault (T2), and the third thermal fault (T3).

20. A method of diagnosing an internal fault of an oil-immersed transformer through composition ratios of dissolved gases, the method comprising:
  a first step of calculating CH4/H2 and C2H2/CH4 in the dissolved gases after extracting the dissolved gases from each of a plurality of transformers of which a type of internal fault is known;
  a second step of setting CH4/H2 and C2H2/CH4, which are indicated depending on each of a thermal fault (T), and a partial discharge (PD) and an energy discharge (D1 or D2) of an electrical fault (E), as x and y coordinates on a fifth xy-plane, so as to classify a whole region of the fifth xy-plane into a thermal fault (T) region, a partial discharge (PD) region, and an energy discharge (D1 or D2) region by using the plurality of x and y coordinates which are set;
a third step of extracting the dissolved gases from insulating oil of the oil-immersed transformer of which the internal fault is able to be diagnosed, so as to calculate CH4/H2 and C2H2/CH4 in the dissolved gases; and
determining the x and y coordinates consisting of CH4/H2 and C2H2/CH4 which are calculated in the third step, so as to determine whether the internal fault of the oil-immersed transformer to be diagnosed is the thermal fault (T), the partial discharge (PD), or the energy discharge (D1 or D2) by using the determined region.

21. The method as claimed in claim 20, wherein in the whole region of the fifth xy-plane, the thermal fault region is 2<CH4/H2 and 0.3<C2H2/CH4, 0.01<C2H2/CH4≤0.3, or 1<CH4/H2 and C2H2/CH4≤0.01, the partial discharge (PD) region CH4/H2≤1 and C2H2/CH4≤0.01, and the energy discharge (D1 or D2) region is CH4/H2≤2 and 0.3<C2H2/CH4.

22. A method of diagnosing an internal fault of an oil-immersed transformer through a composition ratio of dissolved gases, the method comprising:
a first step of calculating C2H4/C2H6 and C2H2/C2H4 in the dissolved gases after extracting the dissolved gases from each of a plurality of transformers of which a type of internal faults is known;
a second step of setting C2H4/C2H6 and C2H2/C2H4, which are indicated depending on each of a partial discharge (PD), a high energy discharge (D1), and a low energy discharge (D2) of an electric fault (E), and a first thermal fault (t<300° C.)(T1), a second thermal fault (300° C.<t<700° C.)(T2), and a third thermal fault (t>700° C.)(T3) of a thermal fault (T) among the internal faults, as x and y coordinates on a sixth xy-plane, so as to classify a whole region of the sixth xy-plane into a partial discharge (PD) region, a low energy discharge (D1) region, a high energy discharge (D2) region, a first thermal fault (t<300° C.)(T1) region, a second thermal fault (300° C.<t<700° C.)(T2) region, and a third thermal fault (t>700° C.)(T3) by using a plurality of coordinates which are set;
a third step of extracting the dissolved gases from insulating oil of the oil-immersed transformer of which the internal fault is able to be diagnosed, so as to calculate C2H4/C2H6 and C2H2/C2H4 in the dissolved gases; and
a fourth step of determining x and y coordinates consisting of C2H4/C2H6 and C2H2/C2H4 which are calculated in the third step, so as to determine whether the internal fault of the oil-immersed transformer to be diagnosed is the partial discharge (PD), the low energy discharge (D1), the high energy discharge (D2), the first thermal fault (t<300° C.)(T1), the second thermal fault (300° C.<t<700° C.)(T2), or the third thermal fault (t>700° C.)(T3) by using the determined region.

23. The method as claimed in claim 22, wherein in a whole region of the sixth xy-plane, the partial discharge (PD) region is C2H4/C2H6≤0.04, or 0.04<C2H4/C2H6≤0.5 and 0.65<C2H2/C2H4, the low energy discharge (D1) region is 0.5<C2H4/C2H6≤1.5 and 0.65<C2H2/C2H4, or 1.5<C2H4/C2H6 and 2.5<C2H2/C2H4, the high energy discharge (D2) region is 1.5<C2H4/C2H6 and 0.65<C2H2/C2H4≤2.5, the first thermal fault region is 0.04<C2H4/C2H6≤1.7 and 0.00025<C2H2/C2H4≤0.01, or 0.04<C2H4/C2H6≤0.8 and 0.01<C2H2/C2H4≤0.65, the second thermal fault region is 1.7<C2H4/C2H6≤4 and 0.0005<C2H2/C2H4≤0.01, 0.8<C2H4/C2H6≤4 and 0.01<C2H2/C2H4≤0.65, or 0.04<C2H4/C2H6≤4 and 0.00005<C2H2/C2H4≤0.00025, and the third thermal fault region is 0.04<C2H4/C2H6≤4 and C2H2/C2H4≤0.00005, 1.7<C2H4/C2H6≤4 and 0.00025<C2H2/C2H4≤0.0005, or 4<C2H4/C2H6 and C2H2/C2H4≤0.65.

* * * * *